(12) United States Patent
Chen et al.

(10) Patent No.: US 11,150,257 B2
(45) Date of Patent: Oct. 19, 2021

(54) SAMPLE RACK LOADING SYSTEM AND LOADING METHOD, AND CHEMILUMINESCENCE DETECTOR

(71) Applicant: Shenzhen New Industries Biomedical Engineering Co., Ltd., Guangdong (CN)

(72) Inventors: Xiaotao Chen, Guangdong (CN); Li Yin, Guangdong (CN); Liang Zhu, Guangdong (CN); Yixian Wang, Guangdong (CN); Xiongjie Zhang, Guangdong (CN); Gang Zhou, Guangdong (CN)

(73) Assignee: Shenzhen New Industries Biomedical Engineering Co., Ltd., Shenzhen (CN)

( * ) Notice: Subject to any disclaimer, the term of this patent is extended or adjusted under 35 U.S.C. 154(b) by 480 days.

(21) Appl. No.: 16/145,237

(22) Filed: Sep. 28, 2018

(65) Prior Publication Data

US 2019/0101557 A1  Apr. 4, 2019

(30) Foreign Application Priority Data

Sep. 29, 2017 (CN) .......................... 201710911681.0

(51) Int. Cl.
*G01N 35/02* (2006.01)
*G01N 35/04* (2006.01)
(Continued)

(52) U.S. Cl.
CPC .......... *G01N 35/026* (2013.01); *G01N 35/04* (2013.01); *A61B 5/00* (2013.01); *B01L 9/06* (2013.01);
(Continued)

(58) Field of Classification Search
CPC ...... G01N 35/026; G01N 35/04; G01N 33/48; G01N 2035/0465; G01N 2035/046;
(Continued)

(56) References Cited

U.S. PATENT DOCUMENTS 5,735,387 A * 4/1998 Polaniec ................ G01N 35/04
198/465.1
6,444,171 B1 * 9/2002 Sakazume .......... G01N 35/0095
422/65

(Continued)

*Primary Examiner* — Benjamin R Whatley
*Assistant Examiner* — Curtis A Thompson
(74) *Attorney, Agent, or Firm* — Gang Yu

(57) ABSTRACT

The present disclosure relates to a sample rack loading system and loading method, and a chemiluminescence detector. The loading system includes: a sample rack storage device, provided with multiple sample holders for storing sample racks; a sample rack transmission device, comprising a rail component and a sample rack block piece mechanism; and a sample rack transfer device, transfers the sample racks between the sample rack storage device and the sample rack transmission device; the sample rack block piece mechanism is configured to block or unblock transmission passages of the rail component; and a guide block is arranged on the sample rack transfer device. When transfer rails of the sample rack transfer device are in abutment with the transmission passages, the guide block drives the sample rack block piece mechanism to unblock the transmission passages.

20 Claims, 19 Drawing Sheets

(51) Int. Cl.
  *B01L 9/06*    (2006.01)
  *G01N 33/48*    (2006.01)
  *A61B 5/00*    (2006.01)

(52) U.S. Cl.
  CPC ... *B01L 2200/18* (2013.01); *B01L 2300/0609* (2013.01); *B01L 2300/123* (2013.01); *G01N 33/48* (2013.01); *G01N 2035/046* (2013.01); *G01N 2035/0465* (2013.01)

(58) Field of Classification Search
  CPC ........ G01N 35/1065; G01N 2035/0418; A61B 5/00; B01L 9/06; B01L 2300/0609; B01L 2200/18; B01L 2300/123
  See application file for complete search history.

(56) References Cited

U.S. PATENT DOCUMENTS

| | | | |
|---|---|---|---|
| 6,790,413 B2 * | 9/2004 | Ngo | G01N 35/026 422/561 |
| 8,252,233 B2 * | 8/2012 | Tokieda | G01N 35/04 422/65 |
| 2015/0160249 A1 * | 6/2015 | Bucher | G01N 35/026 422/65 |
| 2015/0285828 A1 * | 10/2015 | Onizawa | G01N 35/026 73/863.11 |
| 2016/0252634 A1 * | 9/2016 | Hanaya | G01N 35/04 414/222.01 |
| 2017/0030938 A1 * | 2/2017 | She | G01N 35/04 |
| 2017/0067883 A1 * | 3/2017 | Rao | G01N 21/76 |
| 2019/0011471 A1 * | 1/2019 | Abe | G01N 35/00603 |

* cited by examiner

SAMPLE RACK LOADING SYSTEM AND LOADING METHOD, AND CHEMILUMINESCENCE DETECTOR

TECHNICAL FIELD

The present disclosure relates to a technical field of medical appliances, and more particularly, to a sample rack loading system and a loading method, and a chemiluminescence detector.

BACKGROUND

A chemiluminescence detector may perform immunological quantitative analysis on a body fluid sample of a patient, thereby achieving the purpose of inspecting various symptoms such as a cardiovascular disease or an anemia. During analysis, a sample adding arm need to extract a sample from an ample test tube. However, in an existing sample rack loading system, the sample rack is easily skewed and clamped when being loaded and taken out. To arrange a block piece to prevent the sample rack from dropping, a control mechanism needs to be arranged to drive the block piece independently and thus the structure of the block mechanism is complex. Moreover, the control mechanism needs to make a response to unblock a transmission passage and then the sample rack can be transferred. And, the response delay will affect the sample rack loading efficiency.

BRIEF SUMMARY

In view of this, it is necessary to provide a sample rack loading system capable of improving the loading efficiency.

A sample rack loading system includes:

a sample rack storage device, provided with a plurality of sample holders for storing sample racks, each of the sample holders being provided with a delivery port through which each of the sample racks is moved out or moved into;

a sample rack transmission device, including a rail component and a sample rack block piece mechanism; and a sample rack transfer device, provided between the sample rack storage device and the sample rack transmission device so as to transfer the sample racks between the sample rack storage device and the sample rack transmission device;

the sample rack block piece mechanism is arranged at one side, close to the sample rack transfer device, of the rail component; the sample rack block piece mechanism is configured to block or unblock a transmission passage of the rail component; a guide block is arranged on the sample rack transfer device; when transfer a rail of the sample rack transfer device is in abutment joint with the transmission passage, the guide block drives the sample rack block piece mechanism to unblock the transmission passage; and otherwise, the sample rack block piece mechanism blocks the transmission passage.

In some embodiments, each of the sample holders is provided with a block mechanism at the delivery port; the block mechanism includes a first block piece and an elastic piece; the block piece is provided with a first state at which the delivery port is blocked and a second state at which the delivery port is unblocked; the block piece is kept at the first state under an action of the elastic piece; and by pressing against the block piece, the block piece can be placed at the second state.

In some embodiments, the block mechanism further includes a rotary piece; the rotary piece is connected with the sample holder via a hinge piece; and the block piece is extended from one end, close to the delivery port, of the rotary piece to an inside of the delivery port.

In some embodiments, the sample rack transfer device further includes a mounting rack, a rocker arm, a reset component and a sample rack driving mechanism; through the mounting rack, the transfer rail is supported at one side of the delivery port; the rocker arm is rotationally connected to the mounting rack; the rocker arm is provided with a first end and a second end respectively located at two sides of a rotation axial line; the sample rack driving mechanism includes a sample rack grabbing component and a sample rack driving component; the sample rack grabbing component is configured to pick up or release the sample rack; the sample rack driving component is configured to drive the sample rack grabbing component to move under the rocker arm; when the sample rack grabbing component is moved to the first end of the rocker arm, the sample rack grabbing component prods the first end of the rocker arm so that the second end of the rocker arm leaves away from the rotary piece of the block mechanism; and when the sample rack grabbing component leaves away from the first end of the rocker arm, the reset component drives the second end of the rocker arm to press against the rotary piece of the block mechanism.

In some embodiments, a suspension hole is formed at a bottom of each of the sample racks; the sample rack grabbing component includes an electromagnet and an electromagnet ejector rod; and the electromagnet ejector rod can be moved telescopically up and down so as to lock and release a connection with the suspension hole.

In some embodiments, the sample rack transfer device further includes an elastic-pressing rolling shaft mechanism; the elastic-pressing rolling shaft mechanism includes a roller and an elastic pressing piece; the roller is connected with one side of the transfer rail via the elastic pressing piece; and the elastic pressing piece prestresses the roller so that the sample rack passing through the transfer rail is pressed against another side of the transfer rail.

In some embodiments, the reset component is a pressure spring or a tension spring; two ends of the pressure spring or the tension spring are respectively connected with the mounting rack and the rocker arm; and the second end of the rocker arm is pressed against the rotary piece of the block mechanism.

In some embodiments, the sample rack grabbing mechanism is slidably arranged on a guide structure via a sliding seat; and the guide structure is provided on the mounting rack parallel to the transfer rail.

In some embodiments, an abutting inclined surface is provided on a top of the sliding seat; and when the sliding seat is slid to the first end of the rocker arm along the guide structure, the first end of the rocker arm is abutted against the sliding seat and is moved upward along the abutting inclined surface, and the second end of the rocker arm leaves away from the rotary piece of the block mechanism.

In some embodiments, the sample rack block piece mechanism includes a mounting plate, a second block piece and an elastic element; the mounting plate is fixed at one side, close to the sample rack transfer device, of the transmission passage; the block piece is connected with the mounting plate, and the block piece can be moved between a blocking position and a unblocking position relative to the mounting plate; the elastic element is provided between the block piece and the mounting plate, so that the block piece and the mounting plate are elastically connected to place the block piece at the blocking position; and when the sample rack transfer device is in abutment joint with the transmission passage, the guide block is abutted against the block piece to place the block piece at the unblocking position.

Wherein, the blocking position is a position at which the block piece blocks the transmission passage; and the unblocking position is a position at which the block piece unblocks the transmission passage.

In some embodiments, a rolling element is connected outside the block piece and under the transmission passage; slopes are provided at the two sides of the guide block respectively; and when the guide block is translated to pass through the block pieces, the rolling element is abutted against the slopes and is slid along the slopes.

In some embodiments, the block piece is rotationally connected with the mounting plate via a swing arm; and one end of the swing arm is connected with the block piece, and the other end of the swing arm is provided on a rotating shaft of the mounting plate in a sleeving manner.

In some embodiments, the elastic element is a pressure spring or a tension spring; and two ends of the pressure spring or the tension spring are respectively connected with the mounting plate and the swing arm.

In some embodiments, the elastic element is a torsional spring provided on the rotating shaft in a sleeving manner; and the torsional spring is connected with the swing arm.

In some embodiments, the sample rack block piece mechanism includes a plurality of block pieces and swing arms having a same number; the plurality of swing arms are crossly provided on the mounting plate; and a groove is formed at a rotation track overlapped place on the mutually crossed swing arms.

In some embodiments, the mounting plate is provided with a limit element; and the limit element is configured to keep the swing arm at the positions where the block piece blocks the transmission passage.

In some embodiments, the limit element is a limit pin; and the swing arm is rotated around the rotating shaft under an action of the elastic element and is at last abutted against the limit pin.

Correspondingly, an embodiment of the present disclosure further provides a sample rack loading method, which is used for transferring sample racks from a sample rack storage device to a sample rack transmission device via a sample rack transfer device, and the sample rack storage device is provided with a plurality of sample holders for storing the sample racks; each of the sample holders is provided with a delivery port through which each of the sample racks is moved out or moved into; the sample rack transmission device includes a rail component and a sample rack block piece mechanism for blocking a transmission passage of the rail component; the sample rack block piece mechanism includes a block piece and an elastic element; the elastic element drives the block piece to block the transmission passage; the sample rack transfer device includes a transfer rail and a sample rack driving mechanism; the transfer rail can be in abutment joint with the delivery port and/or the transmission passage; and the sample rack loading method includes the following steps:

(a) the sample rack transfer device is moved to one end of the transmission passage of the rail component, so that the transfer rail of the sample rack transfer device is in abutment joint with the transmission passage; and (b) the sample rack driving mechanism transfers the sample racks from the transfer rail to the transmission passage.

In the step (a), the sample rack transfer device is pressed against the block piece that blocks on the transmission passage, so that the block piece unblocks the transmission passage.

In some embodiments, a block mechanism is provided at the delivery port; the block mechanism is provided with a first state at which the delivery port is blocked and a second state at which the delivery port is unblocked; when an elastic force of the elastic element is overcome by pressing against the block piece, the block piece leave away from the delivery port; the sample rack driving mechanism includes a sample rack driving component and a sample rack grabbing component; the sample rack transfer device further includes a rocker arm and a reset component; the rocker arm is provided with a first end and a second end capable of being rotated oppositely; the reset component drives the rocker arm to rotate, so that the second end of the rocker arm is pressed against the block mechanism and the block mechanism is in the second state, wherein the sample rack loading method further includes the following step before the step (a):

(a1) the sample rack transfer device is moved to the sample holders of the sample storage device, so that the transfer rail of the sample rack transfer device is in abutment joint with the delivery port of the sample holder; and in the step (a1), the sample rack driving component keeps the sample rack grabbing component at the first end of the rocker arm, so that the sample rack grabbing component is pressed against the first end of the rocker arm and the second end of the rocker arm leaves away from the block piece mechanism.

In some embodiments, in the step (a1), the sample rack driving component keeps the sample rack grabbing component at the first end of the rocker arm, so that the sample rack grabbing component is pressed against the first end of the rocker arm and the second end of the rocker arm leaves away from the block piece.

In some embodiments, after the step (a1) and before the step (a), the sample rack loading method further includes the following steps:

(a2) the sample rack driving component moves the sample rack grabbing component to be under the sample holders;

(a3) the sample rack grabbing component locks the sample racks in the sample holders; and (a4) the sample rack driving component drives the sample rack grabbing component, thereby transferring the sample racks locked by the sample rack grabbing component to the transfer rail.

In the step (a2) to the step (a4), the sample rack driving component moves the sample rack grabbing component to leave away from the first end of the rocker arm, so that the second end of the rocker arm is pressed against the block piece under the action of the reset component.

An embodiment of the present disclosure further provides a chemiluminescence detector, including the above sample rack loading system.

According to the sample rack loading system provided by the present disclosure, while the transfer rail of the sample rack transfer device is in abutment joint with the transmission passage of the rail component, the guide block on the sample rack transfer device drives the sample rack block piece mechanism blocking the transmission passage to unblock a passage for transferring the sample racks, and an independent control mechanism does not need to be arranged to regulate and control the conditions of the transmission passage; and thus the response delay among structural components in each part is prevented from affecting the efficiency of loading the sample racks.

DETAILED DESCRIPTION

In order to understand the present disclosure conveniently, the present disclosure will be described below more comprehensively with reference to relevant accompanying drawings. Preferred embodiments of the present disclosure are given in the accompanying drawings. However, the present disclosure may be implemented in many different forms and is not limited to the embodiments described herein. On the contrary, the purposes for providing these embodiments are to understand the contents disclosed in the present disclosure more completely and thoroughly.

It is to be noted that, when an element is "fixed" on another element, it may be directly on another element or also may has a middle element. When an element is "connected" to another element, it may be directly connected to another element or may be simultaneously has a middle element. As used herein, the terms "inside", "outside", "left", "right" and similar expressions are only for illustration but not express a unique embodiment.

By simultaneously referring to FIG. 1 to FIG. 4, a sample rack loading system includes a sample rack storage device 100, a sample rack transmission device 300 and a sample rack transfer device 200. The sample rack transfer device 200 is arranged between the sample rack storage device 100 and the sample rack transmission device 300, so as to implement the transfer of sample racks 400 between the sample rack storage device 100 and the sample rack transmission device 300.

Figure 5:
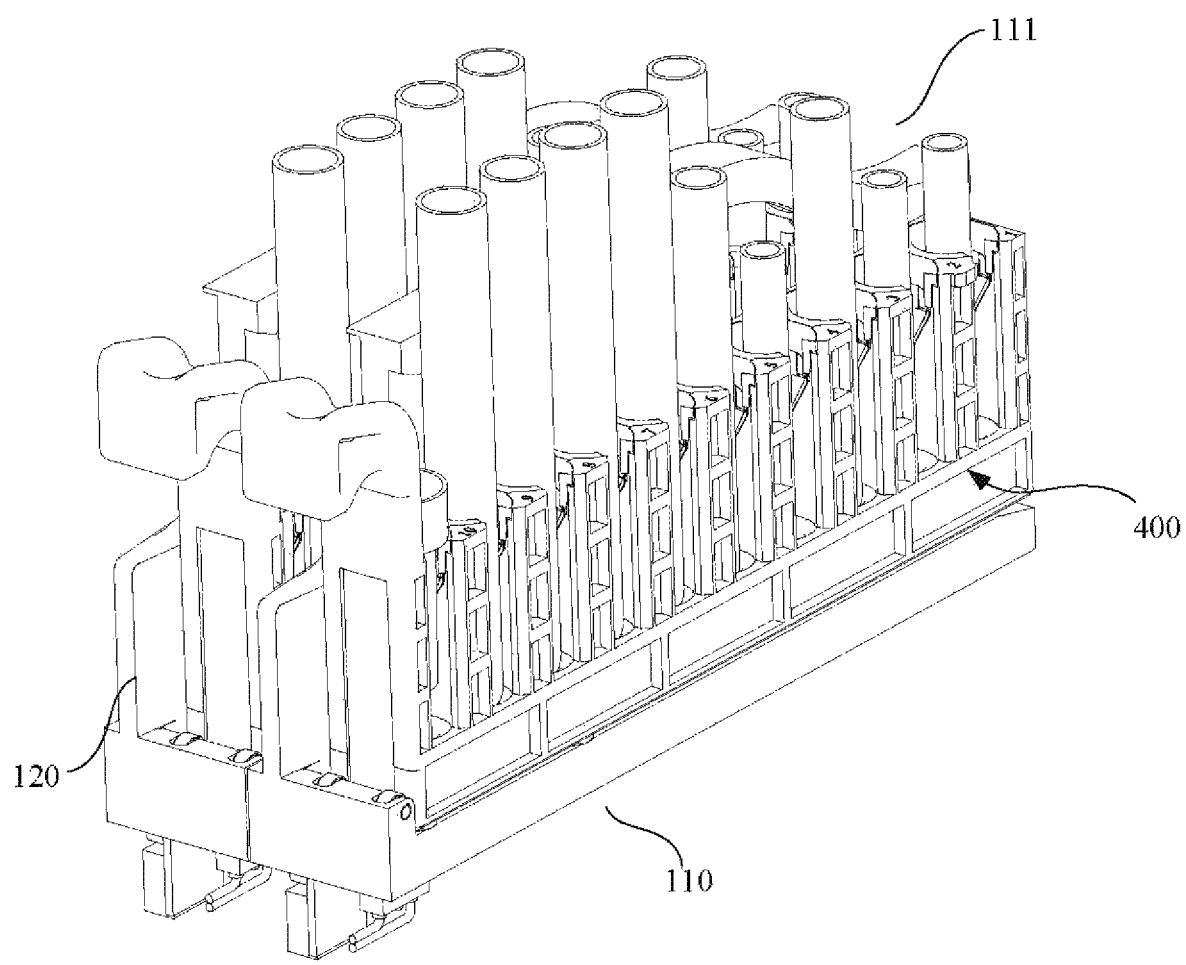
FIG. 5 is a structural schematic diagram of a sample rack loaded in a sample holder.
Figure 6:
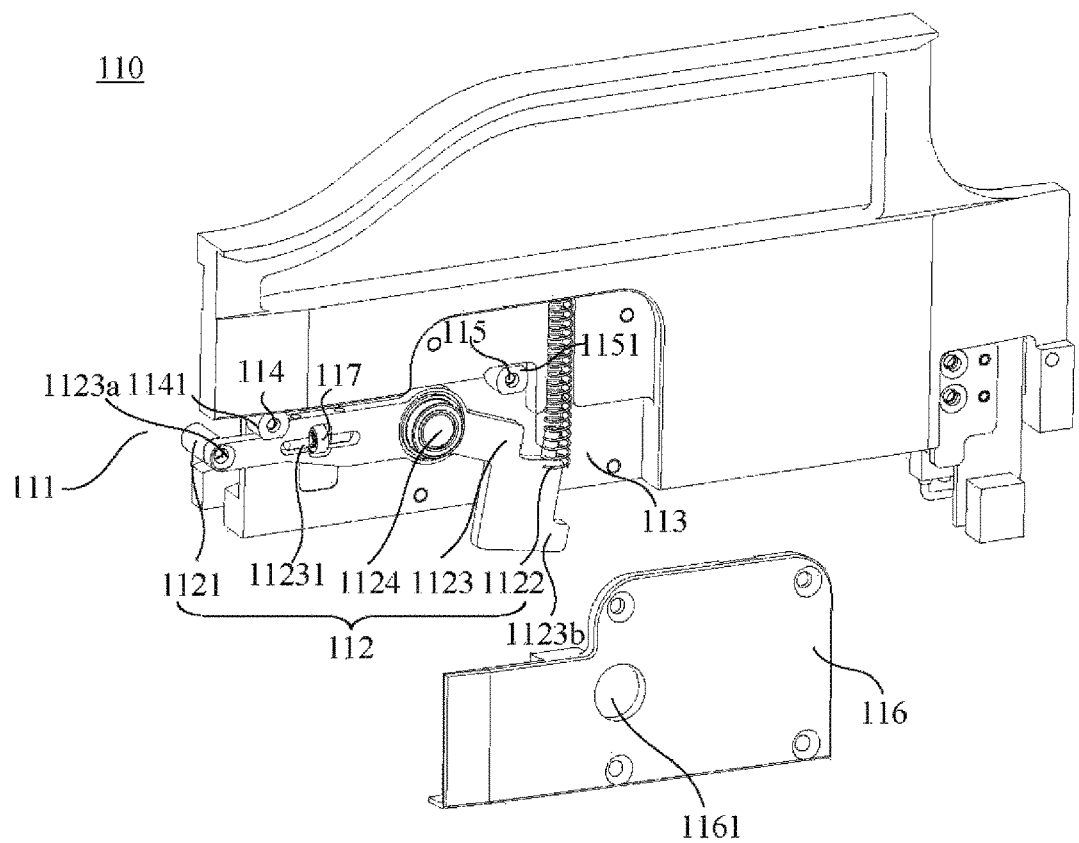
FIG. 6 is a structural decomposition schematic diagram of a sample holder in one embodiment.

With reference to FIG. 5 and FIG. 6, in some embodiments, the sample rack storage device 100 includes a sample holder 110, configured to store the sample racks 400. The sample holder 110 is provided with a delivery port 111 through which the sample racks 400 are moved out or moved into. A block mechanism 112 is arranged at the delivery port 111 of the sample holder 110. In some embodiments, the block mechanism 112 includes a block piece 1121 and an elastic piece; the block piece 1121 is provided with a first state at which the delivery port 111 is blocked and a second state at which the delivery port 111 is unblocked. The elastic piece is configured to keep the block piece 1121 at the first state. Through pressing against the block piece 1121 and overcoming the elastic force of the elastic piece, the block piece 1121 may be placed at the second state. It may be understood that, under a condition in which there is no external force to press against the block piece 1121, the elastic piece may keep the block piece 1121 at the first state, that is, the block piece 1121 blocks the delivery port 111 of the sample holder 110. Therefore, the sample racks 400 are prevented from sliding from the sample holder 110. In addition, when the sample racks 400 are loaded at one side 120, far away from the delivery port 111, of the sample holder 110, the block piece 1121 may prevent the sample racks 400 from being pushed out from the delivery port 111 of the sample racks 400. Furthermore, when the sample racks 400 are loaded into the sample holder 110, the sample racks 400 may be abutted against the block piece 1121, so that the sample racks 400 can be accurately placed into the sample holder 110 and the efficiency of loading the sample racks 400 to the sample holder 110 is greatly improved.

In above embodiment, the switching of the block piece 1121 between the first state and the second state may be implemented in various ways. The specific structure of the block mechanism 112 will be further described below by implementing the switching of the block piece 1121 between the first state and the second state in a rotary manner.

Referring to FIG. 6, in some embodiments, the block mechanism 112 further includes a rotary piece 1123 and a hinged piece 1124; the rotary piece 1123 is rotationally connected to the sample holder 110 via the hinged piece 1124; and the block piece 1121 is extended out from one end 1123a (hereinafter referred to as the first end 1123a), close to the delivery port 111, of the rotary piece 1123 and is located at the delivery port 111. When the rotary piece 1123 is rotated around the hinged piece 1124 relative to the sample holder 110, the block piece 1121 is also rotated around the hinged piece 1124 correspondingly, and through the rotation effect, the block piece 1121 may be switched between the first state and the second state; and under the driving of the elastic piece, the rotary piece 1123 is rotated around the hinged piece 1124 and at last the block piece 1121 is kept at the first state at which the delivery port 111 is blocked. The hinged piece 1124 which implements the rotation of the rotary piece 1123 relative to the sample holder 110 may be of a shaft pin structure and also may be of a bearing structure.

In some embodiments, the hinged piece 1124 is located between the block piece 1121 and the elastic piece. The two ends of the elastic piece are respectively abutted against the rotary piece 1123 and the sample holder 110; and when being stressed externally, the elastic piece may be compressed to allow the rotation of the rotary piece 1123 around the hinged piece 1124, so that the rotary piece 1123 drives the block piece 1121 to move to the second state.

Specifically, referring to FIG. 6, in this embodiment, the elastic piece is a pressure spring 1122. The pressure spring 1122 is downwardly pressed against one end 1123b (hereinafter referred to as the second end 1123b), far away from the block piece 1121, of the rotary piece 1123, so that the block piece 1121 at the other end of the rotary piece 1123 is moved to the first state. When a counter-acting force is applied on the rotary piece 1123 to sufficiently overcome the pressure spring 1122, the rotary piece 1123 drives the block piece 1121 to move from the first state to the second state and thus the delivery port 111 of the sample holder 110 is unblocked.

In another some embodiments, the elastic piece further may be a tension spring and is located between the block piece 1121 and the hinged piece 1124. The two ends of the tension spring are respectively connected with the rotary piece 1123 and the sample holder 110. When the external force overcomes the tensile force of the tension spring and the tension spring is stretched, the rotary piece 1123 is rotated around the hinged piece 1124 and thus the block piece 1121 is driven to move to the second state.

In the above embodiment, both the pressure spring and the tension spring are only specific applications of the elastic piece in some embodiments. Of course, the elastic piece also may be a rod with elastic bending or shrinking property, which will not be illustrated one by one.

Referring to FIG. 6, in some embodiments, a mounting groove 113 is formed on the sidewall of the sample holder 110; a first limit piece 114 and a second limit piece 115 are arranged in the mounting groove 113. The first limit piece 114 and the second limit piece 115 are arranged on a track that the rotary piece 1123 is rotated around the hinged piece 1124, so that the amplitude that the rotary piece 1123 is rotated around the hinged piece 1124 is limited in a certain range. In addition, a buffer pad further may be arranged on each of the limit pieces, so as to buffer the collision force with the limit pieces when the rotary piece 1123 is rotated.

Specifically, in some embodiments, the first limit piece 114 and the second limit piece 115 may be of a rod-like structure, on which a first buffer pad 1141 and a second buffer pad 1151 are arranged respectively in a sleeving manner. It may be understood that, in order to implement the effect that the block piece 1121 on the rotary piece 1123 may be switched between the first state and the second state, the first limit piece 114 and the second limit piece 115 may be arranged as follows: when the rotary piece 1123 is rotated around the hinged piece 1124 to abut against the first limit piece 114, the block piece 1121 is in the first state; and when the rotary piece 1123 is rotated around the hinged piece 1124 to abut against the second limit piece 115, the block piece 1121 is in the second state. In this embodiment, through the arranged mounting groove 113, the block mechanism 112 is assembled conveniently, and the block mechanism 112 can be prevented from stretching out from the side of the sample holder 110 to affect the storage effect of the sample racks 400 in the sample holder 110. Moreover, by arranging the block mechanism 112 in the mounting groove 113 on the sidewall, the space occupation may be reduced.

Referring to FIG. 6, in some embodiments, the sample holder 110 is connected with a cover plate 116 at the mounting groove 113, so as to hold the block mechanism 112 between the cover plate 116 and the sample holder 110. A mounting hole 1161 is formed on the cover plate 116. One end of the hinged piece 1124 is connected with the sample holder 110, and the other end of the hinged piece 1124 is spliced into the mounting hole 1161 on the cover plate 116. The second end 1123b, far away from the delivery port 111, of the rotary piece 1123 is stretched out from the bottom of the sample holder 110. By pressing or prodding the second end 1123b of the rotary piece 1123, the rotary piece 1123 may be rotated around the hinged piece 1124, and thus the block piece 1121 connected to the rotary piece 1123 is switched between the first state and the second state.

Referring to FIG. 6, in some embodiments, a rolling element 117 is arranged between the block piece 1121 and the hinged piece 1124 on the rotary piece 1123. The rolling element 117 is abutted against the sample holder 110, so that when the rotary piece 1123 is rotated around the hinged piece 1124, the rolling element 117 is rolled along a rotation track relative to the sample holder 110, and thus the friction between the rotary piece 1123 and the sample holder 110 when the rotary piece 1123 is rotated is prevented, the rotation effect is smoother and the structural stability of the block mechanism 112 is prevented from being damaged due to long-term friction. It may be understood that the rolling element 117 may be a rolling ball or a rolling bearing. Correspondingly, a hole position 11231 for mounting the rolling element 117 may be formed on the rotary piece 1123.

Figure 7:
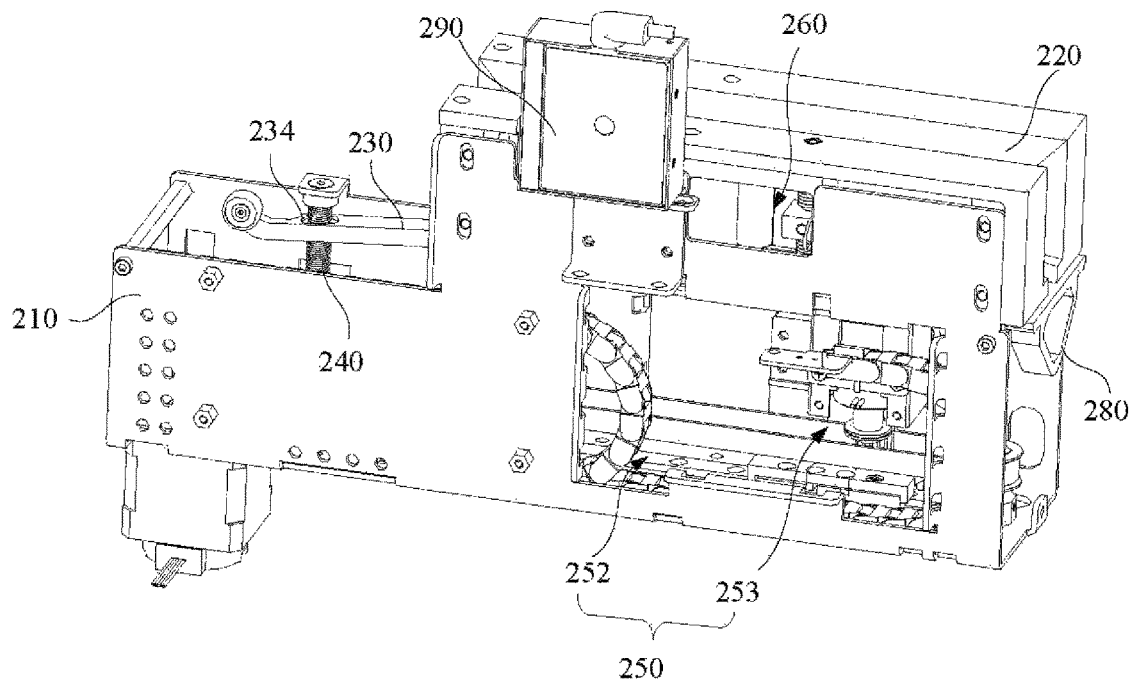
FIG. 7 is a structural schematic diagram of a sample rack transfer device in one embodiment.

Referring to FIG. 7, in some embodiments, the sample rack transfer device 200 includes a mounting rack 210, a transfer rail 220, a rocker arm 230, a reset component and a sample rack driving mechanism 250. Through the mounting rack 210, the transfer rail 220 is supported at one side of the delivery port 111 of the sample holder 110, so that a passage for transmitting the sample racks 400 may be formed between the transfer rail 220 and the delivery port 111 of the sample holder 110. The rocker arm 230 is rotationally connected to the sidewall of the mounting rack 210 and can be rotated around a rotation axial line. By arranging one end of the rocker arm 230 under the block mechanism 112, when the rocker arm 230 is rotated around the rotation axial line, the block mechanism 112 may be driven to move from the first state to the second state, thereby unblocking the delivery port 111 of the sample holder 110 and thus the sample racks 400 may be transferred between the sample holder 110 and the transfer rail 220. Specifically, the reset component is configured to drive the rocker arm 230 to rotate around the rotation axial line, so that the rocker arm 230 drives the rotary piece 1123 of the block mechanism 112 to rotate around the hinged piece 1124, thus driving the block piece 1121 to move to the second state. It may be understood that, when the rocker arm 230 does not apply the force to the rotary piece 1123, the rotary piece 1123 is rotated around the hinged piece 1124 under the action of the elastic piece, so as to move the block piece 1121 and keep it in the first state. In other words, through the rocker arm 230, the state in which the block piece 1121 of the block mechanism 112 is may be selected, so as to selectively unblock or block the passage for the sample racks 400 between the sample holder 110 and the transfer rail 220. Specifically, when the block piece 1121 is in the first state, since the block piece 1121 blocks the delivery port 111 of the sample holder 110, the sample racks 400 cannot be moved into or moved out of the sample holder 110 and the block piece 1121 takes the blocking effect at this moment. When the block piece 1121 is in the second state, since the block piece 1121 does not block the delivery port 111 of the sample holder 110, the sample rack driving mechanism 250 may drive the sample racks 400 to transfer between the sample holder 110 and the transfer rail 220. It is to be noted that, a sensor may be correspondingly arranged on the transfer rail 220 to detect whether the sample racks 400 are moved into or moved out or not. It may be understood that, in some embodiments, according to the technical solutions of the present disclosure in the art, a position for detecting the sample racks 400 and transmission conditions are provided in some structures, which will not be repeated here.

Figure 1:
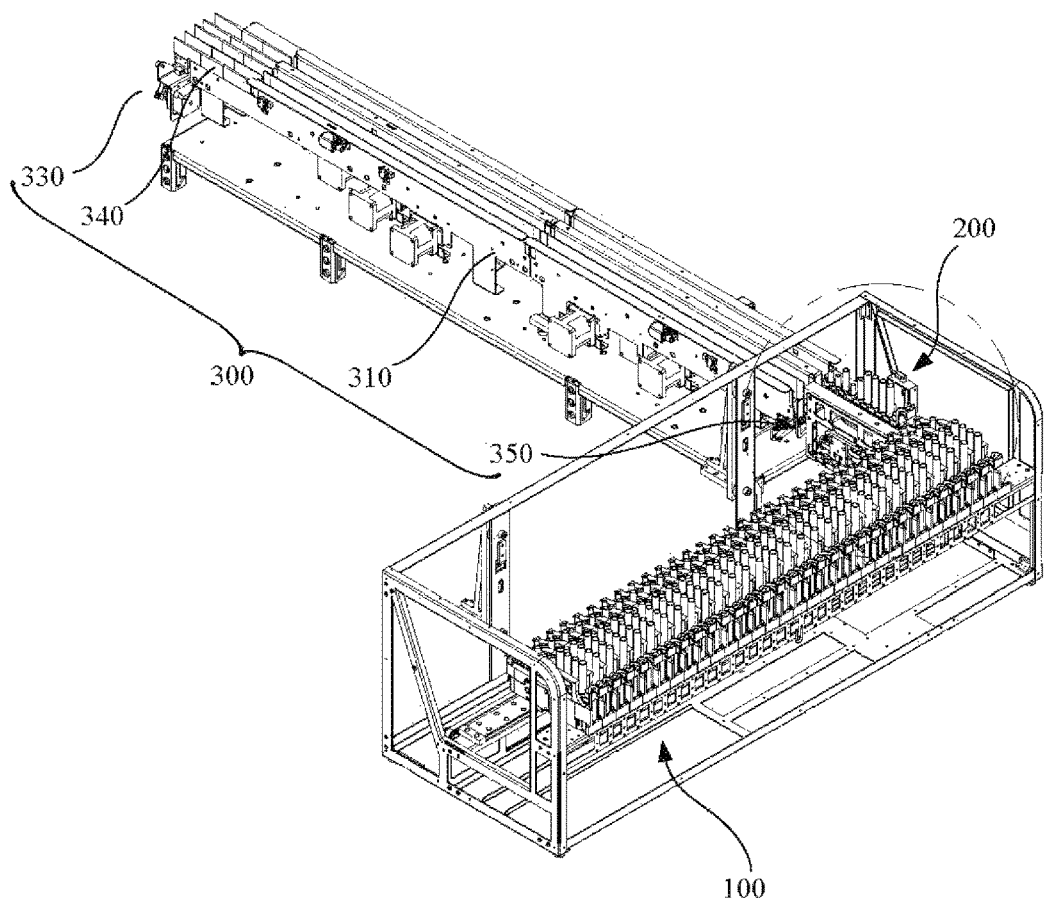
FIG. 1 is a structural schematic diagram of a sample rack loading system in one embodiment.
Figure 2:
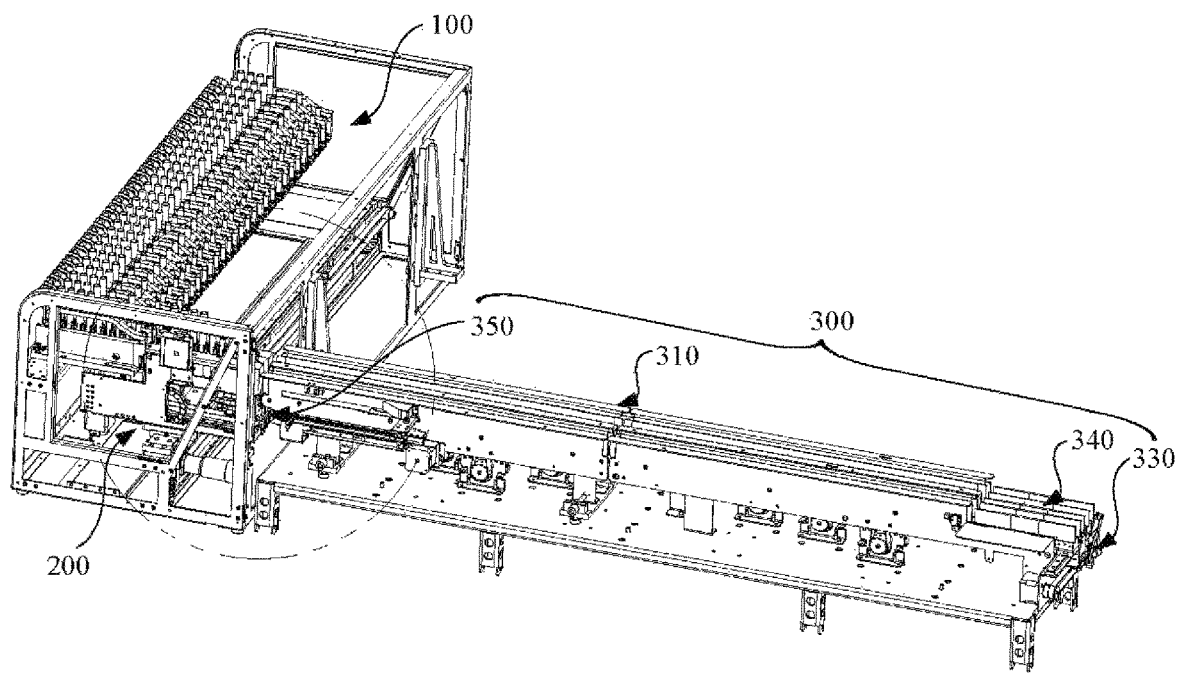
FIG. 2 is a structural schematic diagram of a sample rack loading system at another viewing angle in one embodiment.
Figure 3:
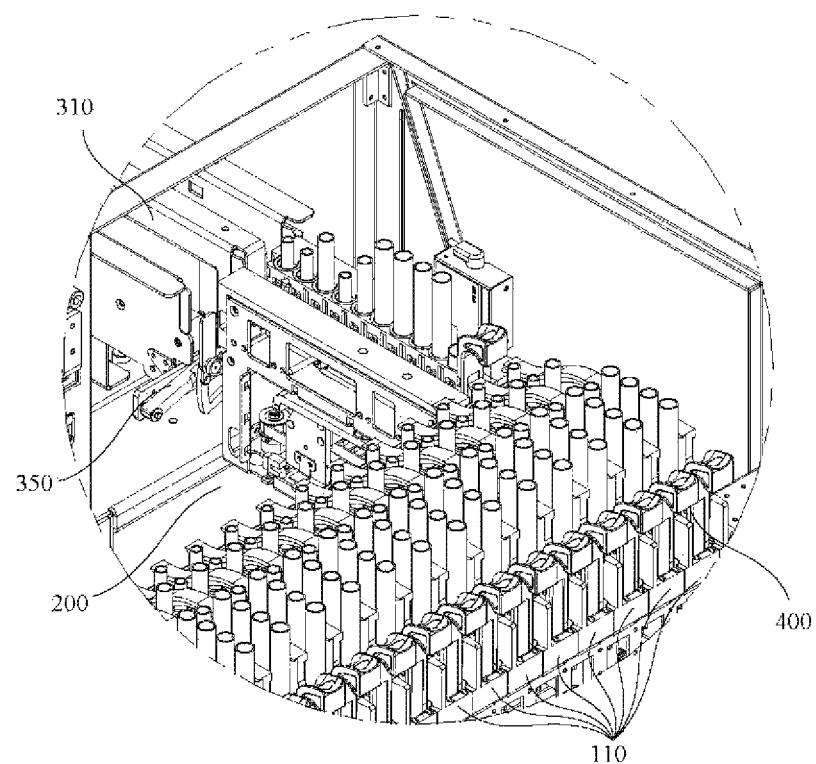
FIG. 3 is a partial enlarged diagram of a partial structure of a circle in FIG. 1.
Figure 4:
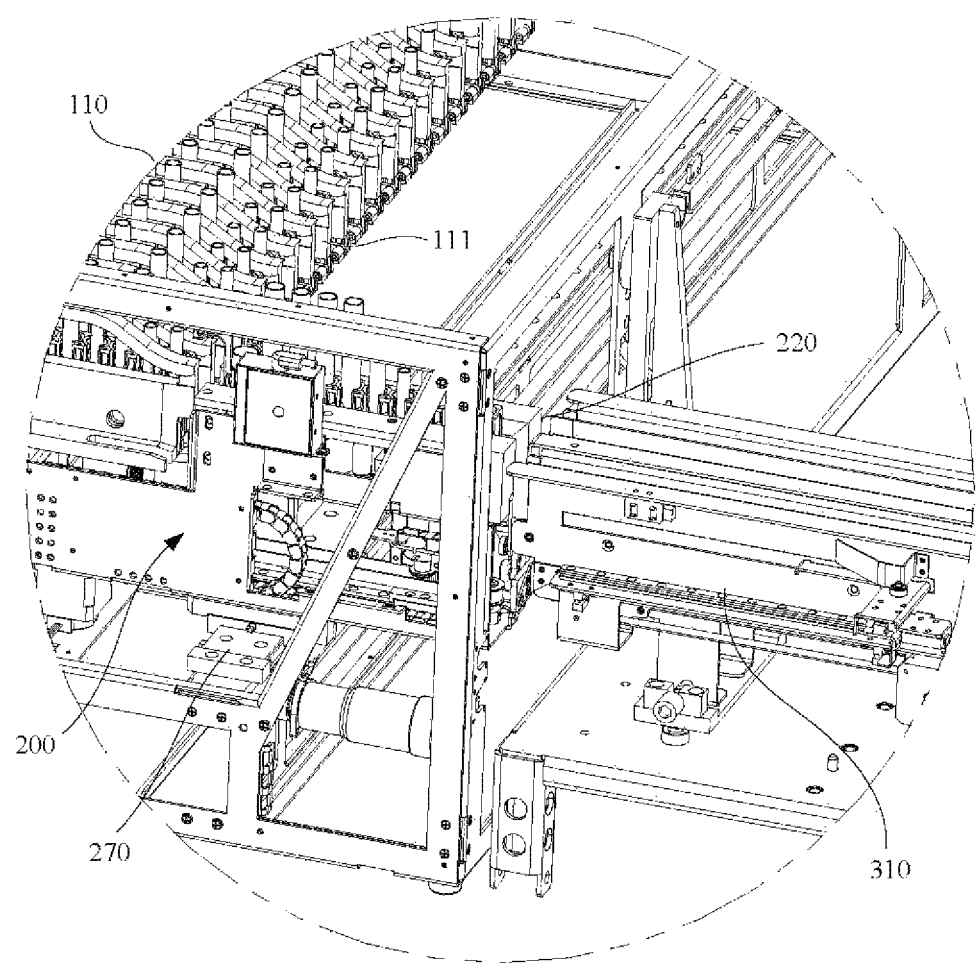
FIG. 4 is a partial enlarged diagram of a partial structure of a circle in FIG. 2.

Referring to FIG. 4, in some embodiments, the sample rack storage device 100 includes a plurality of sample holders 110. The sample rack transfer device 200 may be in abutment joint with the plurality of sample holders 110 of the sample rack storage device 100 so as to implement the transfer of the sample racks 400 on the multiple sample holders 110. It is to be noted that, when the transfer rails 220 of the sample rack transfer device 200 cannot be adjusted in a transmission direction, in order to take out and place into the sample racks 400 in the plurality of sample holders 110, the delivery ports 111 of the plurality of sample holders 110 may be arranged at one side facing to the transfer rails 220 in parallel. In this embodiment, the sample rack transfer device 200 further includes a transfer component 270. The transfer component 270 is configured to move the mounting rack 210, so that the transfer rails 220 on the mounting rack 210 are respectively in abutment joint with the delivery ports 111 of the plurality of sample holders 110.

Figure 9:
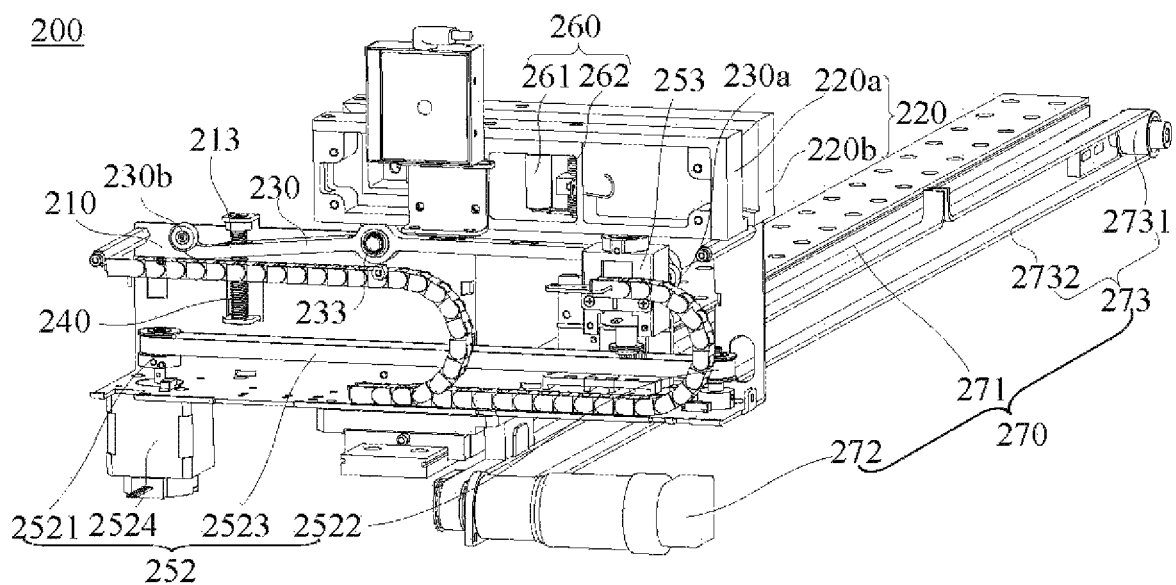
FIG. 9 is an internal structural schematic diagram of a sample rack transfer device in one embodiment.

Specifically, referring to FIG. 9, the transfer component 270 includes a translation guide rail 271 and a driving motor 272. The translation guide rail 271 is extended transversely along the delivery ports 111 of the plurality of sample holders 110. The mounting rack 210 is slidably connected to the translation guide rail 271. The driving motor 272 is in transmission with the mounting rack 210 via a screw rod component or a belt component. With a transmission manner of the belt component as an example, the belt component 273 includes a synchronizing wheel 2731 and a driving wheel belt 2732, and the driving wheel belt 2732 is arranged on an output shaft of the driving motor 272 and the synchronizing wheel 2731 in a sleeving manner. In this way, when the driving motor 272 is rotated forwardly or reversely, the mounting rack 210 may be driven by the driving wheel belt 2732 to move along the translation guide rail 271, and thus the transfer rail 220 is in abutment joint with the delivery port 111 of each of the sample holders 110 of the sample rack storage device 100.

Figure 8:
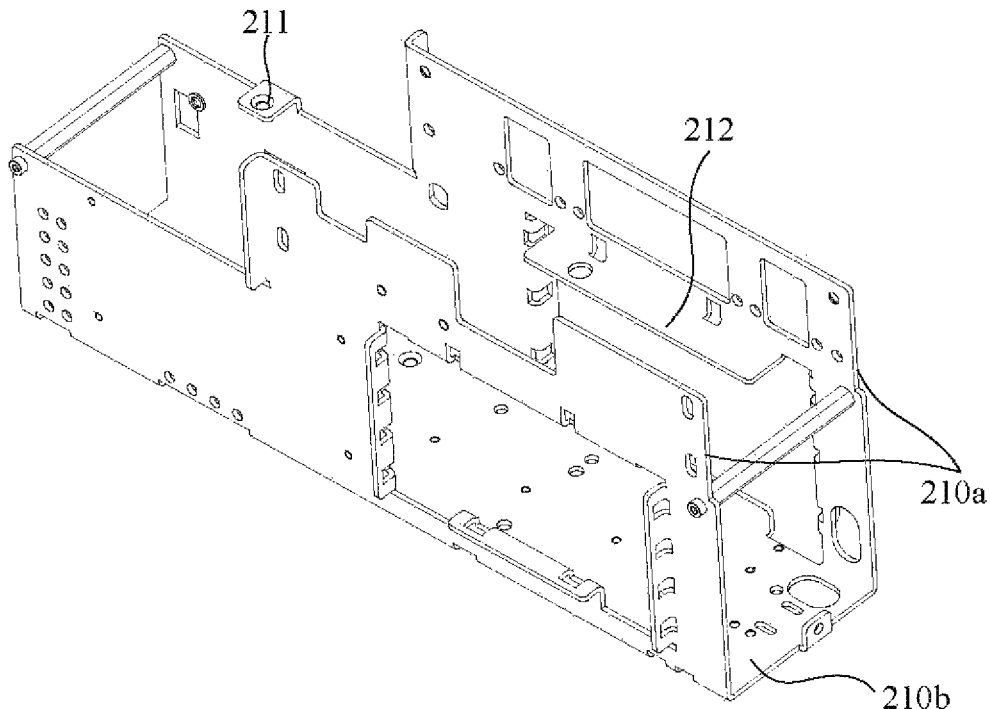
FIG. 8 is a structural schematic diagram of a mounting rack in one embodiment.

With reference to FIG. 8 and FIG. 9, the mounting rack 210 includes two sidewalls 210a and a bottom wall 210b connected to bottoms of the sidewalls 210a. The two sidewalls 210a and the bottom wall 210b are enclosed into a mounting space so as to hold the structures such as the rocker arm 230, the transfer rail 220 and the driving mechanism 250. The transfer rail 220 is mounted on the sidewalls 210a of the mounting rack 210. In this embodiment, a routing plate 212 is arranged on the inner surface of each of the sidewalls 210a of the mounting rack 210 so as to route conveniently. Moreover, through the routing plates 212, the strength of the mounting rack 210 may be strengthened.

Referring to FIG. 9, in some embodiments, an elastic-pressing rolling shaft mechanism 260 is arranged inside the transfer rail 220. The elastic-pressing rolling shaft mechanism 260 is configured to abut sample racks 400 slid through the transfer rail 220 against one side of the transfer rail 220, so as to eliminate a gap between the sample racks 400 and the side of the transfer rail 220 and guarantee the relative dimensional accuracy of the sample racks 400 on the transfer rail 220 along the direction of the translation guide rail 271, and thus the sample racks 400 are stably moved along the transfer rail 220. Moreover, through the elastic pressing, the sample racks 400 are prevented from rushing out of the transfer rail 220 due to the too fast speed during the transfer process. Specifically, the elastic-pressing rolling shaft mechanism 260 includes a roller 261 and an elastic-pressing piece 262. The roller 261 is connected to one side 220a of the transfer rail 220 via the elastic-pressing piece 262, and under the action of the elastic-pressing piece 262, is abutted against the other side 220b of the transfer rail 220. It may be understood that, the elastic-pressing piece 262 may be a torsional spring or a pressure spring, and also may be an elastomer made of an elastic material.

Referring to FIG. 9, the rocker arm 230 implements the rotary connection with the mounting rack 210 via a bearing 233. The rocker arm 230 is provided with a first end 230a and a second end 230b respectively located at two sides of the bearing 233. The reset component is a pressure spring 240. The two ends of the pressure spring 240 are respectively connected with the mounting rack 210 and the rocker arm 230. To be exact, the two ends of the pressure spring 240 are abutted against between the mounting rack 210 and the rocker arm 230. The second end 230b of the rocker arm 230 is rotated around the bearing 233 under the pressing action of the pressure spring 240, thereby driving the rotary piece 1123 to rotate around the hinged piece 1124 so that the block piece 1121 is moved to the second state.

Figure 10:
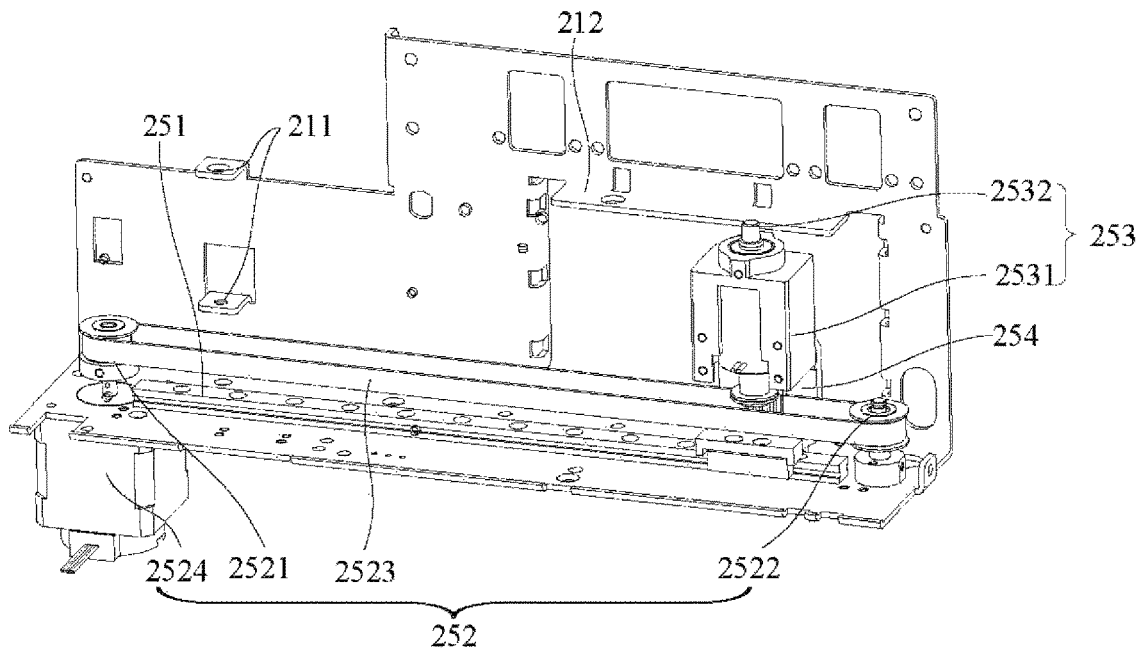
FIG. 10 is a structural schematic diagram of a sample rack grabbing component and a sample rack driving component in one embodiment.

Simultaneously referring to FIG. 9 and FIG. 10, in the above embodiment, a spring guide rod mounting plate 211 is arranged on the mounting rack 210. A spring guide rod 213 is fixed on the spring guide rod mounting plate 211. By arranging the pressure spring 240 on the spring guide rod 213 in a sleeving manner, the pressure spring 240 is prevented from deviating an axial line during telescopic movement and thus the pressure spring 240 is axially applied to a rocker arm 230 to obtain relatively good elastic performance. It is to be noted that, with reference to FIG. 7, a perforation hole 234 may be formed on the rocker arm 230 so as to movably sleeve the swing arm 230 to the spring guide rod 213 and thus the pressure spring 240 is abutted against the perforation hole 234 of the rocker arm 230.

Figure 11:
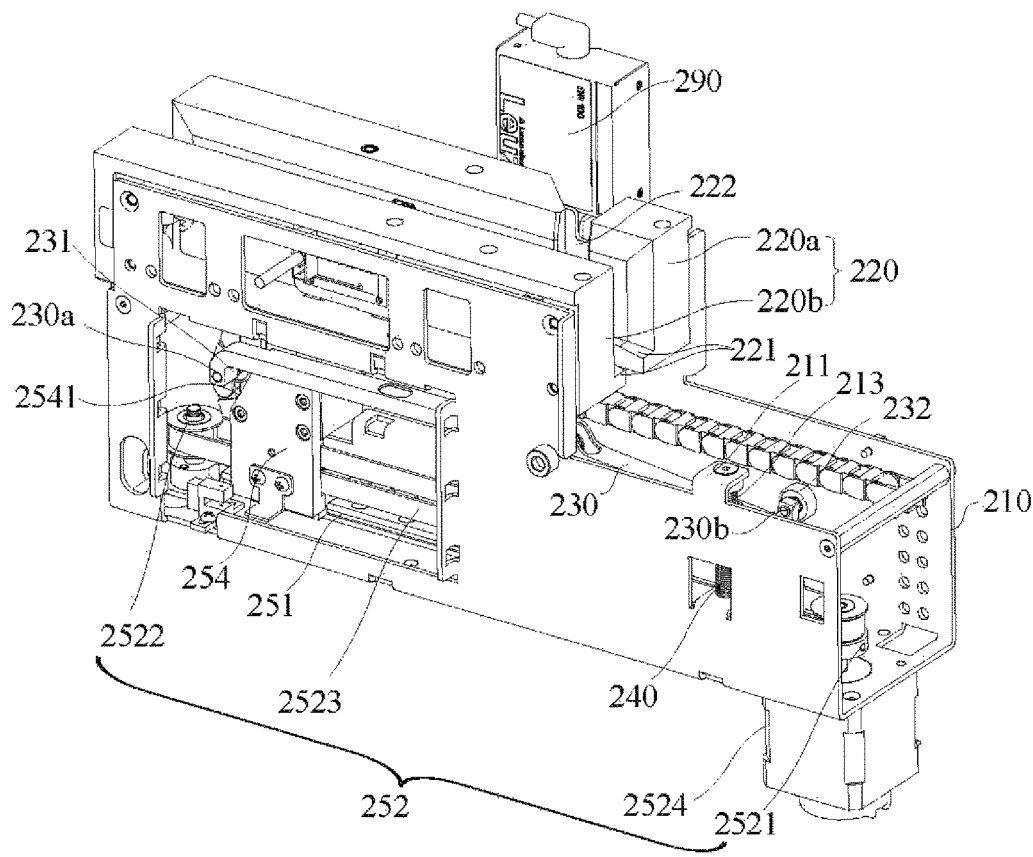
FIG. 11 is a structural schematic diagram of a sample rack transfer device at another viewing angle in one embodiment.

Referring to FIG. 11, in some embodiment, in order to enable the sample racks 400 to pass through the transfer rail 220 conveniently, the transfer rail 220 is provided with a guide port 221. A notch 222 for enabling a code scanner 290 to scan sample information in the sample racks 400 is formed on the transfer rail 220.

Simultaneously referring to FIG. 9 and FIG. 10, in some embodiments, the sample rack driving mechanism 250 includes a guide structure, a sample rack driving component 252 and a sample rack grabbing component 253. The guide structure is arranged on the mounting rack 210 parallel to the transfer rail 220. The sample rack driving component 252 is configured to drive the sample rack grabbing component 253 to move along the guide structure. The sample rack grabbing component 253 is configured to grab or release the sample racks 400. Since the guide structure is parallel to the transfer rail 220, when the sample rack driving component 252 drives the sample rack grabbing component 253 to move along the guide structure, the sample rack grabbing component 253 may move the sample racks 400 into the transfer rail 220 or move the sample racks 400 out of the transfer rail 220. It may be understood that, the guide structure is a linear guide rail 251 arranged on the bottom wall 210b of the mounting rack 210 or a guide sliding groove formed on the inner surface of the sidewall 210a of the mounting rack 210.

With reference to FIG. 11, in the above embodiment, the sample rack grabbing component 253 is slidably connected with the linear guide rail 251 via a sliding seat 254. An abutting inclined surface 2541 is formed on the top of the sliding seat 254. When the sample racks 400 are not moved by the sample rack grabbing component 253, the sample rack driving component 252 moves the sample rack grabbing component 253 via the sliding seat 254 to the first end 230a of the rocker arm 230. At this moment, since the first end 230a of the rocker arm 230 moves upward along the abutting inclined surface 2541 of the sliding seat 254 so that the rocker arm 230 is rotated around the bearing 233, when the first end 230a of the rocker arm 230 is pressed upward by the sliding seat 254, the second end 230b of the rocker arm 230 is rotated downward around the bearing 233 to leave away from the rotary piece 1123 of the block mechanism 112; and thus the rotary piece 1123 propels the block piece 1121 to move to the first state with the elastic force of the pressure spring 1122 without the pressing of the rocker arm 230. By blocking the delivery port 111 of the sample holder 110, the sample racks 400 are prevented from slipping out from the delivery port of the sample holder 110.

In above embodiment, when the sliding seat 254 leaves away the first end 230a of the rocker arm 230 along a linear guide rail 251, that is to say, there is no external force pressing against the first end 230a of the rocker arm 230 upward, the second end 230b of the rocker arm 230 is pressed against the rotary piece 1123 of the block mechanism 112 upward under the driving of the pressure spring 240, so that the rotary piece 1123 overcomes the elastic force of the pressure spring 1122 and is rotated relative to the hinged piece 1124, thereby driving the block piece 1121 to move to the second state.

Referring to FIG. 11, in some embodiments, the first end 230a of the rocker arm 230 is provided with a first rolling bearing 231, and the second end 230b of the rocker arm 230 is provided with a second rolling bearing 232. Therefore, in the process when the sliding seat 254 is pressed against the first end 230a of the rocker arm 230 upward, the first rolling bearing 231 rolls along the abutting inclined surface 2541 of the sliding seat 254. Correspondingly, in the process when the second end 230b of the rocker arm 230 is pressed against the rotary piece 1123 of the block mechanism 112 upward, the relative movement between the second rolling bearing 232 and the rotary piece 1123 is the rolling. Compared with the sliding manner, the rolling manner has a small friction force. Moreover, thanks to such a structure, the surface rolling contact is implemented, so that the relative movement among the rocker arm 230, the sliding seat 254 and the rotary piece 1123 is smoother.

Figure 5A:
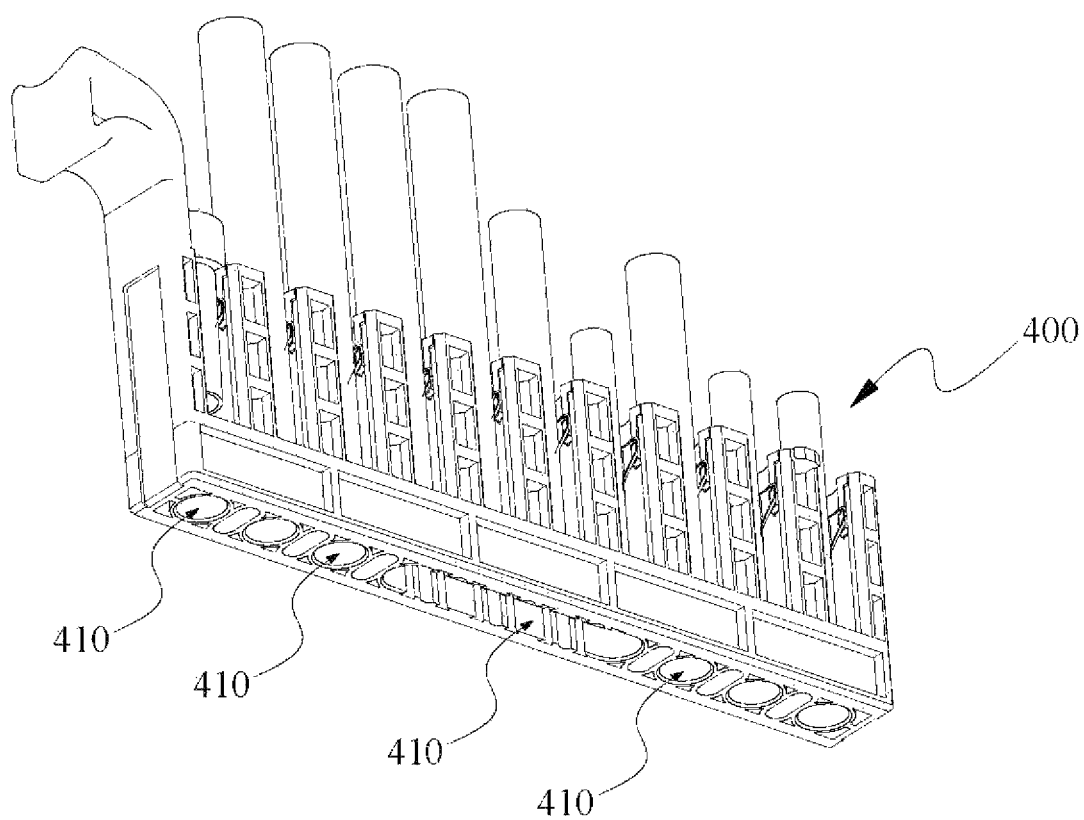
FIG. 5a is a structural schematic diagram of a sample rack loaded in a sample holder at another viewing angle.

Simultaneously referring to FIG. 5a, FIG. 9 and FIG. 10, in some embodiments, the sample rack driving component 252 includes a driving wheel 2521, a driven wheel 2522, a synchronous belt 2523 and a motor 2524. The driving wheel 2521 is mounted on an output shaft of the motor 2524, the driven wheel 2522 is fixed on the mounting rack 210 and the synchronous belt 2523 is arranged on the driving wheel 2521 and the driven wheel 2522 in a sleeving manner. By connecting the sliding seat 254 with the synchronous belt 2523, when the motor 2524 drives the driving wheel 2521 to rotate, the synchronous belt 2523 drives the sliding seat 254 to move along the guide structure. The sample rack grabbing component 253 is mounted on the sliding seat 254, and is moved with the sliding seat 254 along the guide structure. Specifically, the sample rack grabbing component 253 includes an electromagnet 2531 and an electromagnet ejector rod 2532; and the electromagnet ejector rod 2532 can move telescopically up and down so as to lock or release the connection with the sample racks 400. It may be understood that, a suspension hole 410 is formed at the bottom of each of the sample racks 400, so that the electromagnet ejector rod 2532 may be stretched out and drawn back at the suspension holes 410 and thus the sample racks 400 are grabbed or released. Of course, the sample rack grabbing component 253 also may grab or release the sample racks 400 in other manners, for example, using a cylinder with a telescopic property.

With reference to FIG. 2, FIG. 3, FIG. 12 and FIG. 13, in some embodiments, the sample rack transmission device 300 includes a rail component 310, a transmission block mechanism 330, a rail changing mechanism 340 and a sample rack block piece mechanism 350. Specifically, the transmission block mechanism 330 and the rail changing mechanism 340 are fixed at one side of the rail component 310 via the mounting seat 320. Wherein, the transmission block mechanism 330 is configured to block the sample racks 400 in transmission passages of the rail component 310 so as to prevent the sample racks 400 from slipping out from the transmission passages of the rail component 310, and the rail changing mechanism 340 is configured to transfer the sample racks 400 among plurality of transmission passages of the rail component 310 so that the sample racks 400 are transmitted in different transmission passages. The sample rack block piece mechanism 350 is arranged at the other side of the rail component 310 and is located between the sample rack transfer device 200 and the rail component 310. The sample rack block piece mechanism 350 is configured to block or unblock the transmission passages of the rail component 310. Specifically, when the sample racks 400 are not transferred between the sample rack transfer device 200 and the rail component 310, the sample rack block piece mechanism 350 blocks the transmission passages of the rail component 310 so as to prevent the sample racks from slipping out from the rail component 310. When the sample racks 400 need to be transferred between the sample rack transfer device 200 and the rail component 310, the sample rack transfer device 200 will drive the sample rack block piece mechanism 350 to unblock the transmission passages of the rail component 310 so as to pass through the sample racks 400.

Figure 12:
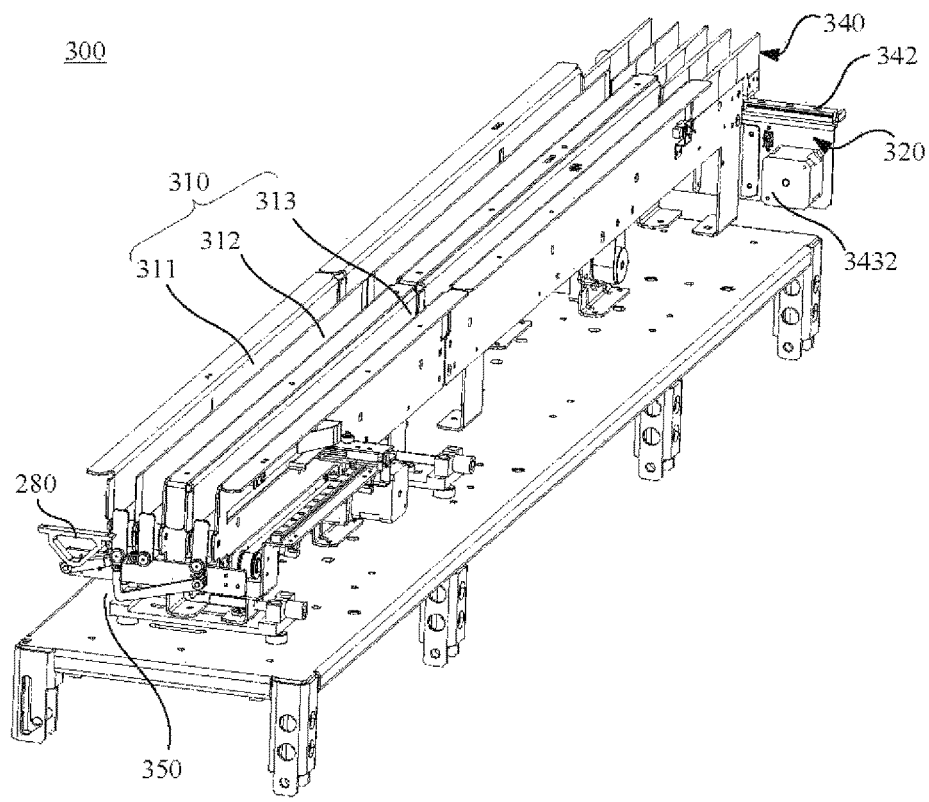
FIG. 12 is a structural schematic diagram of a rail component in one embodiment.

It may be understood that, in the above embodiment, when the sample racks 400 are transferred, the sample rack transfer device 200 drives the sample rack block piece mechanism 350 to unblock the transmission passages of the rail component 310 in various ways. Specifically, when there is an only need to abut the transfer rail 220 of the sample rack transfer device 200 with the transmission passages of the rail component 310, the sample rack transfer device 200 may remove structures, blocked at the transmission passages, of the sample rack block piece mechanism 350. As shown in FIG. 7 and FIG. 12, a guide block 280 is arranged on the sample rack transfer device 200. When the transfer rail 220 of the sample rack transfer device 200 is abutted with the transmission passages, the guide block 280 drives the sample rack block piece mechanism 350 to unblock the transmission passages. It is to be noted that, the guide block 280 is used as a structure of driving the sample rack block piece mechanism 350 and there may be multiple selections for its mounting position. As shown in FIG. 7, the guide block 280 is mounted below the transfer rail 220, so that when the sample rack transfer device 200 transversely moves relative to the rail component 310 (moves on a transmission direction perpendicular to the rail component), the guide block 280 may transversely pass through the sample rack block piece mechanism 350 and thus the structures blocked at the transmission passages are removed, thereby unblocking the transmission passages.

In the above embodiment, the transfer rail 220 is abutted with the transmission passages, which refers to that relative positions of the transfer rail 220 and the transmission passages are in a state at which the sample racks 400 may be transferred between transfer rail 220 and the transmission passages. As shown in FIG. 12, when the transfer rail 220 of the sample rack transfer device 200 is not abutted with the transmission passages of the rail component 310, the guide block 280 arranged on the sample rack transfer device 200 does not drive the sample rack block piece mechanism 350. At this moment, the sample rack block piece mechanism 350 blocks the transmission passages of the rail component 310, so as to prevent the sample racks 400 in the transmission passages from slipping out from the rail component 310. Correspondingly, in order to implement the effect that the sample racks 400 are transferred between the sample rack transfer device 200 and the rail component 310, there is a need to place the sample rack block piece mechanism 350 in a state of unblocking the transmission passages when the transfer rail 220 is abutted with the transmission passages. Specifically, as shown in FIG. 14 to FIG. 17, under a condition in which the rail component 310 is provided with plurality of transmission passages, when the transfer rail 220 is abutted with any transmission passage in the rail component 310, the guide block 280 on the sample rack transfer device 200 drives the sample rack block piece mechanism 350 to unblock corresponding transmission passage abutted with the transfer rail 220. In other words, through abutting the sample rack transfer device 200 with each transmission passage, the transmission passage abutted with the sample rack transfer device 200 can be unblocked, and thus there is no need to arrange independent driving structure and corresponding control device.

Referring to FIG. 14 to FIG. 17, in some embodiments, the sample rack block piece mechanism 350 includes a mounting plate 351, block pieces 352 and elastic elements; the mounting plate 351 is fixed at the sides, close to the sample rack transfer device 200, of the transmission passages; the block pieces 352 are connected with the mounting plate 351, and the block pieces 352 can be moved between a block position and an unblock position relative to the mounting plate 351; the elastic elements are arranged between the block pieces 352 and the mounting plate 351, so that the block pieces 352 and the mounting plate 351 are elastically connected to place the block pieces 352 at the block position; when the transfer rail 220 is abutted with the transmission passages, the guide block 280 is abutted against the block pieces 352 to place the block pieces 352 at the unblock position. Wherein, the block position is a position at which the block pieces 352 block the transmission passages, and the unblock position is a position at which the block pieces 352 unblock the transmission passages.

In some embodiment, the block pieces 352 are rotationally connected with the mounting plate 351 via swing arms 355; one ends of the swing arms 355 are connected with the block pieces 352, and the other ends of the swing arms 355 are arranged on the rotating shafts of the mounting plate 351 in a sleeving manner. Through the swing arms 355, arms by which the guide block 280 applies a force onto the block pieces 352 may be prolonged, so that the guide block 280 conveniently overcomes the force of the elastic elements on the block pieces 352 to smoothly press the block pieces 352.

In some embodiments, limit elements are arranged on the mounting plate 351. The limit elements are configured to keep the swing arms 355 at position where the block pieces 352 block the transmission passages. The block pieces 352 are prevented from excessively stretching out of the transmission passages under the action of the elastic elements to interfere with other structures. Moreover, the limit elements may limit the elastic elements at a state having an initial deformation. In this way, when the guide block 280 leaves away with the sample rack transfer device 200, the elastic elements have a larger elastic restoring force and the block pieces 352 are quickly restored to a state in which the transmission passages are blocked.

In some embodiment, each of the limit elements may be a limit pin. The swing arms 355 are rotated around the rotating shafts under the action of the elastic elements to finally abut against the limit pins. Each of the elastic elements may be a pressure spring or a tension spring; and the two ends of the pressure springs or the tension springs are respectively connected with the mounting plate 351 and the swing arms 355. Of course, the elastic elements also may be torsional springs arranged on the rotating shafts in a sleeving manner; the torsional springs are connected with the swing arms 355. The torsional springs are arranged in a rotating space in which the swing arms 355 are rotated around the rotating shafts relative to the mounting plates 351, and the space occupation of the elastic elements is small.

In some embodiments, the sample rack block piece mechanism 350 includes plurality of block pieces 352 and swing arms 355 having the same number; the plurality of swing arms 355 are crossly arranged on the mounting plate 351; and grooves are formed at rotation track overlapped places on the mutually crossed swing arms 355 so as to avoid the mutual interference. By crossly arranging the swing arms 355, the length of the arms of the swing arms 355 are increased, so that the guide lock 280 drives the swing arms 355 to overcome the elastic force of the elastic elements and to rotate around the rotating shafts, and thus the block pieces 352 are guaranteed to be removed to unblock the transmission passages of the rail component 310.

It is to be noted that, the number of the block pieces 352 of the sample rack block piece mechanism 350 may be adjusted according to transmission passages, in need of being blocked actually, of the rail component 310. The structure of the sample rack block piece mechanism 350 will be further described below in detail with three transmission passages of the rail component 310 as an example.

With reference to FIG. 14 to FIG. 17, in some embodiments, the rail component 310 includes a first transmission passage 311, a second transmission passage 312 and a third transmission passage 313; correspondingly, the sample rack block piece mechanism 350 includes a first block piece 3521, a second block piece 3522, a third block piece 3523, a first swing arm 3551, a second swing arm 3552 and a third swing arm 3553; one ends of the first swing arm 3551, the second swing arm 3552 and the third swing arm 3553 are connected respectively with the first block piece 3521, the second block piece 3522 and the third block piece 3523, the other ends of the first swing arm 3551 and the third swing arm 3553 are rotationally connected with a first rotating shaft 3561 on the mounting plate 351 and the other end of the second swing arm 3552 is rotationally connected to a second rotating shaft 3562 on the mounting plate 351. The first swing arm 3551 and the third swing arm 3553 both are rotationally connected with the mounting plate 351 via the first rotating shaft 3561 and thus the number of rotating shafts is reduced. In addition, the first swing arm 3551 and the second swing arm 3552 are crossly arranged and a groove 3554 is formed on the second swing arm 3552, so that the first swing arm 3551 and the second swing arm 3552 are rotationally moved relative to the mounting seat 351 without interference, and the first block piece 3521 and the second block piece 3522 may be respectively removed from the first transmission passage 311 and the second transmission passage 312 by the guide block 280.

With reference to FIG. 18 to FIG. 26, in the above embodiment, a first torsional spring 3531 and a second torsional spring 3532 are respectively arranged on the first rotating shaft 3561 and the second rotating shaft 3562 in a sleeving manner; the first torsional spring 3531 elastically presses the first swing arm 3551 and the third swing arm 3553 to abut against a first limit pin 3571 and a third limit pin 3573. In other words, the first swing arm 3551 and the third swing arm 3553 both implement the rotation around the first rotating shaft 3561 via the first torsional spring 3531. With such a structure, the installation space is saved and more swing arms 355 and block pieces 352 are arranged as much as possible in the limited installation space of the mounting plate 351.

In the above embodiment, the guide block 280 unblocks a passage between the transfer rail 220 and the transmission passage by driving the block piece 352 blocked at the transmission passage abutted with the transfer rail 220 and the block pieces 352 blocked at other transmission passages are not affected. Specifically, referring to FIG. 15 to FIG. 17, when the transfer rail 220 is abutted with the first transmission passage 311, the guide block 280 is abutted against the first block piece 3521 to place the first block piece 3521 at the unblock position; when the transfer rail 220 is abutted with the second transmission passage 312, the guide block 280 is abutted against the second block piece 3522 to place the second block piece 3522 at the unblock position; and when the transfer rail 220 is abutted with the third transmission passage 313, the guide block 280 is abutted against the third block piece 3523 to place the third block piece 3523 at the unblock position.

Referring to FIG. 19 to FIG. 26, in some embodiments, the guide block 280 transversely passes through each transmission passage of the rail component 310 with the sample rack transfer device 200, driving the block piece 352 blocked at the transmission passage abutted with the transfer rail 220 of the sample rack transfer device 200 and thus unblocking the transmission passage abutted with the transfer rail 220. Specifically, rolling pieces are connected outside the block pieces 352 and below the transmission passages; slopes 281 are arranged at two sides of the guide block 280; when the guide block 280 is translated to pass through the block pieces 352, the rolling pieces are abutted against the slopes 281 and are slid along the slopes 281. The guide block 280 may be transversely and smoothly moved from one sides of the block pieces 352; and meanwhile, through the pressing of the guide block 280 to the rolling pieces, the block pieces 352 leave away from the transmission passages. It may be understood that, the rolling pieces may be rollers 354 connected to the block pieces 352 via shaft pins in a rolling manner.

Figure 13:
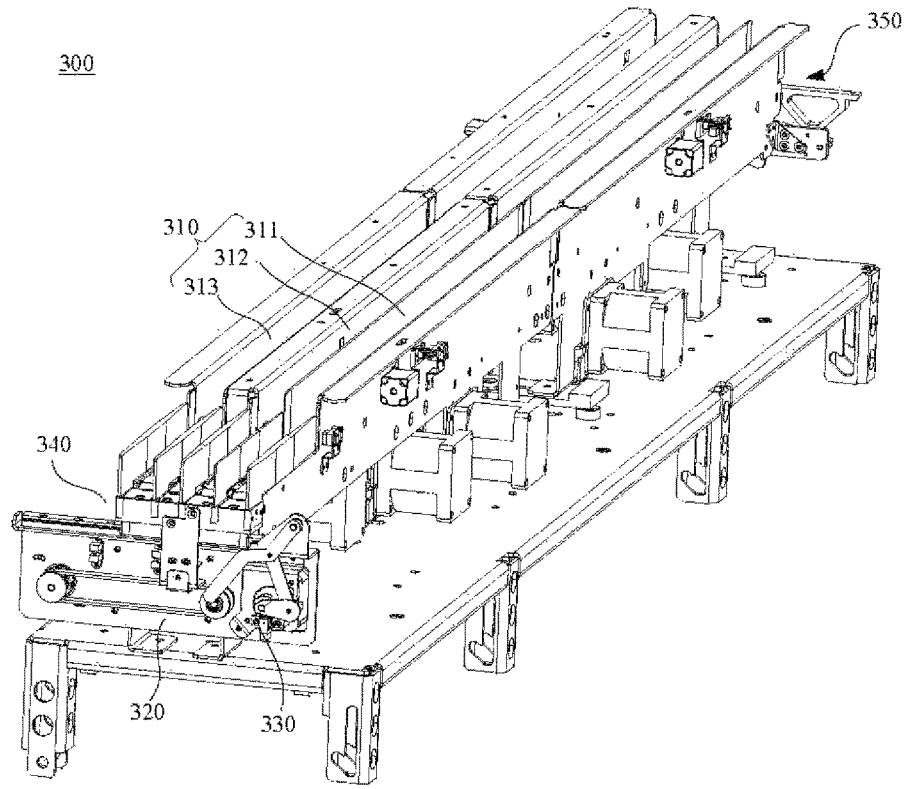
FIG. 13 is a structural schematic diagram of a rail component at another viewing angle in one embodiment.
Figure 14:
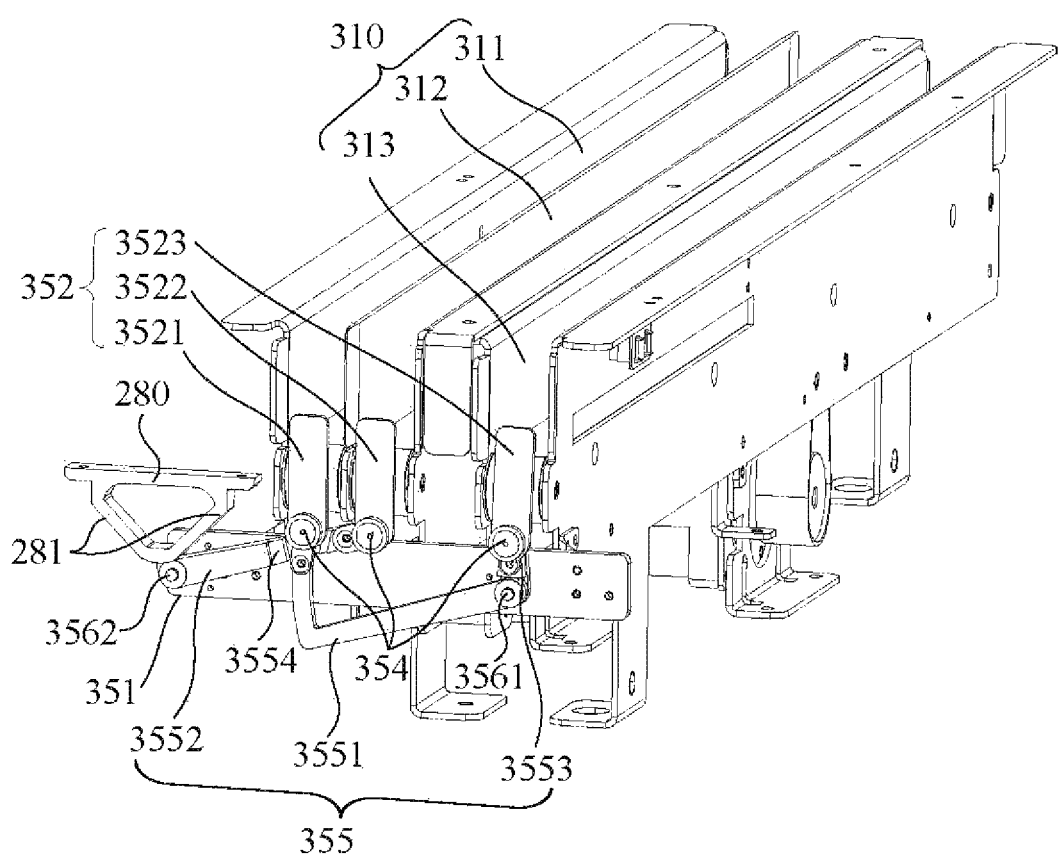
FIG. 14 is a schematic diagram showing a guide block is moved transversely from a left side in one embodiment.
Figure 15:
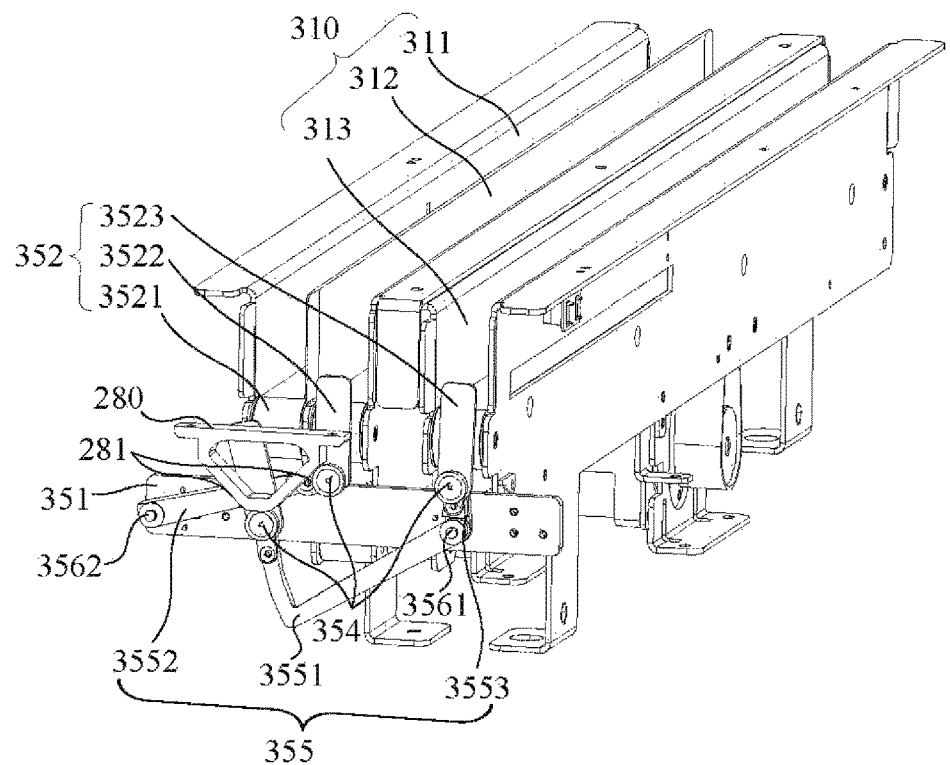
FIG. 15 is a schematic diagram showing a guide block drives away a first block piece in one embodiment.
Figure 16:
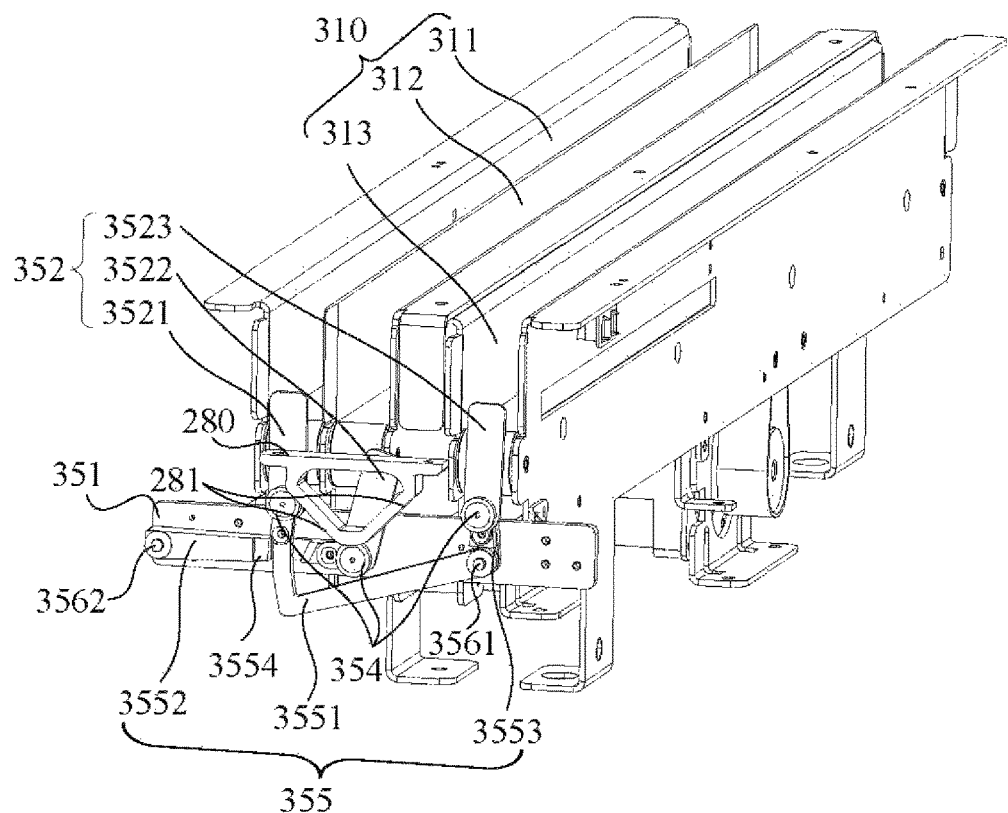
FIG. 16 is a schematic diagram showing a guide block drives away a second block piece in one embodiment.
Figure 17:
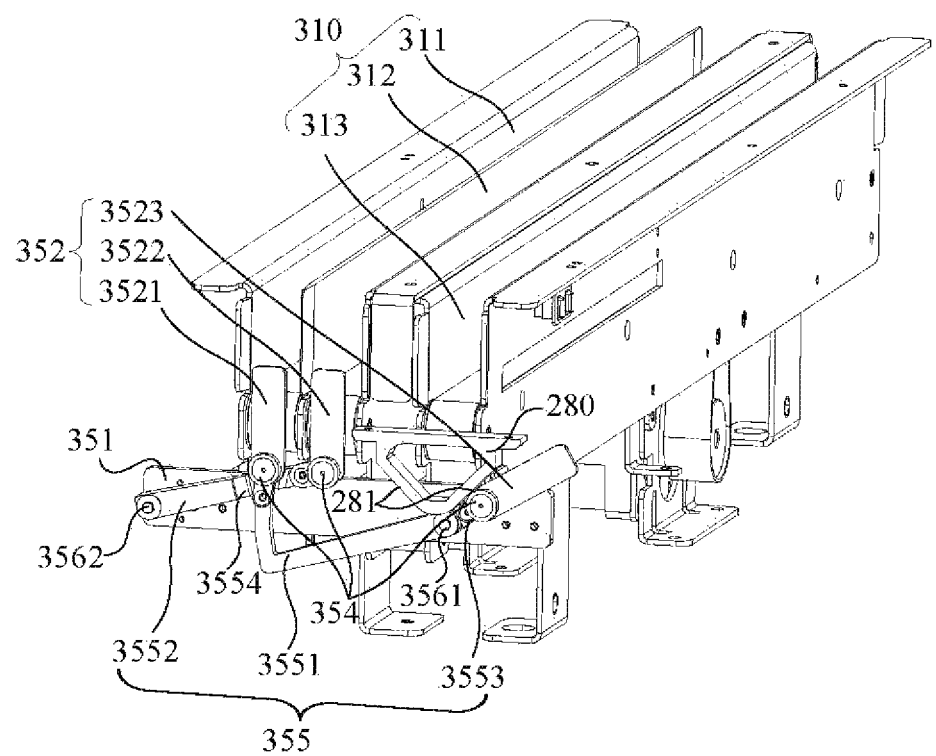
FIG. 17 is a schematic diagram showing a guide block drives away a third block piece in one embodiment.
Figure 18:
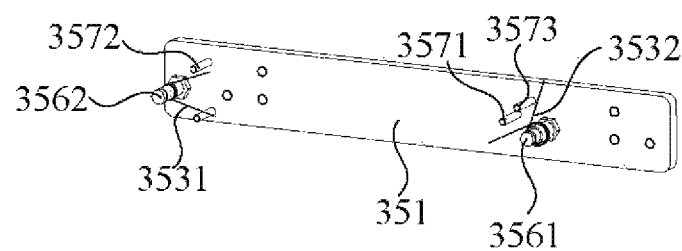
FIG. 18 is a schematic diagram of a mounting structure among a rotating shaft, a torsional spring and a mounting plate in one embodiment.
Figure 19:
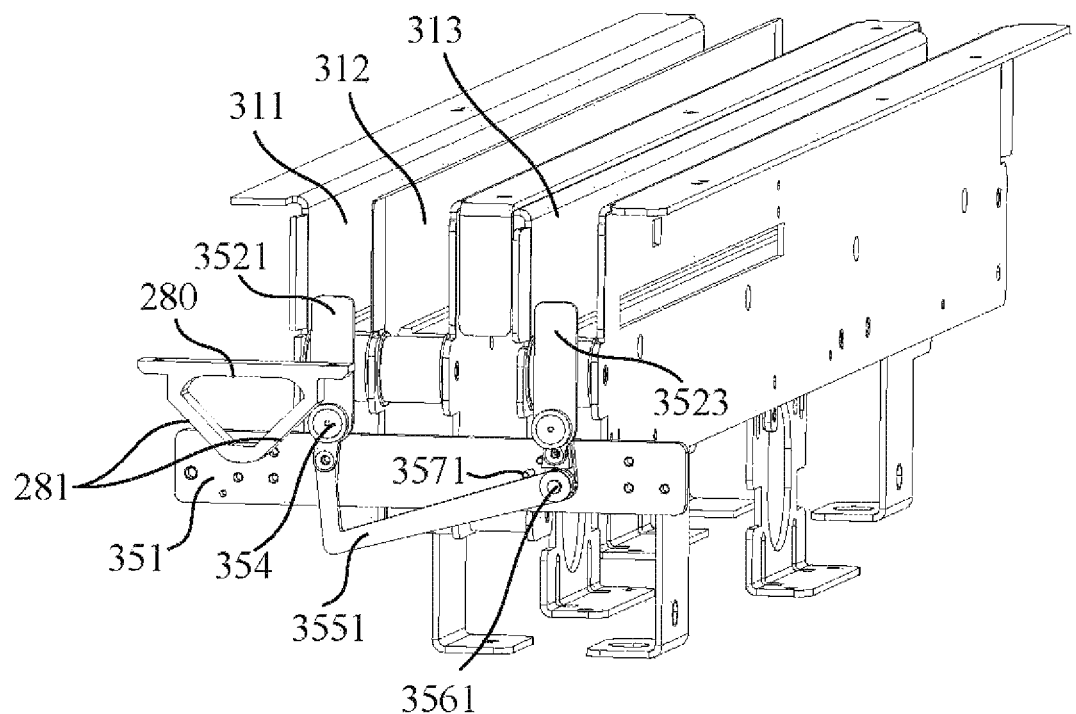
FIG. 19 is a schematic diagram showing a guide block is abutted against a roller from a left side of a first block piece in one embodiment.
Figure 20:
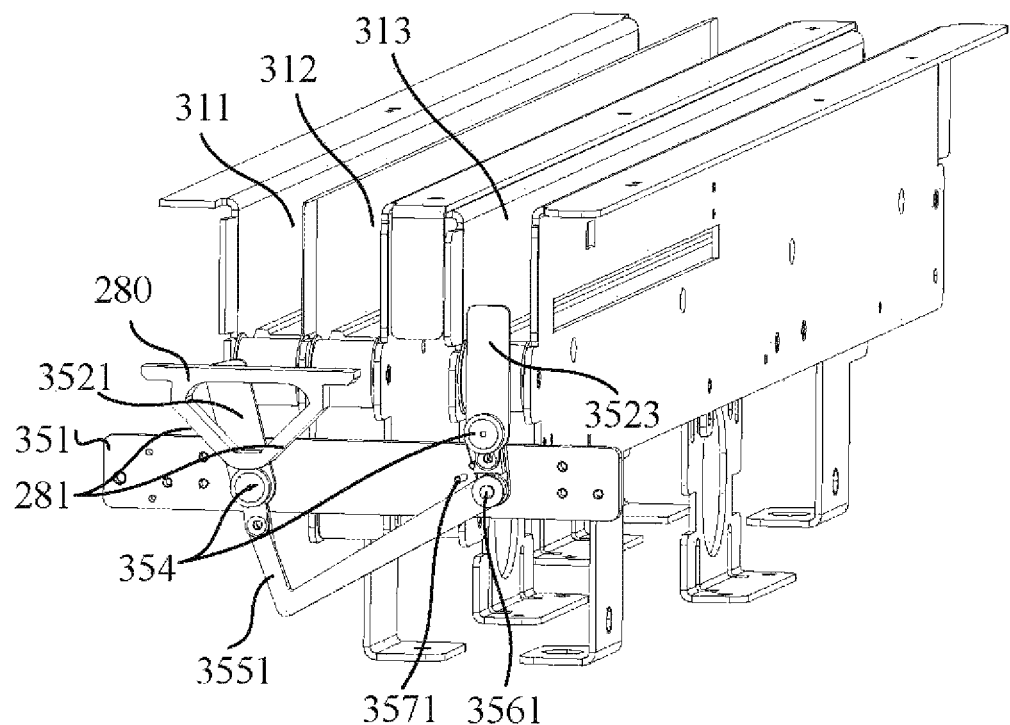
FIG. 20 is a schematic diagram showing a guide block is pressed against a first block piece in one embodiment.
Figure 21:
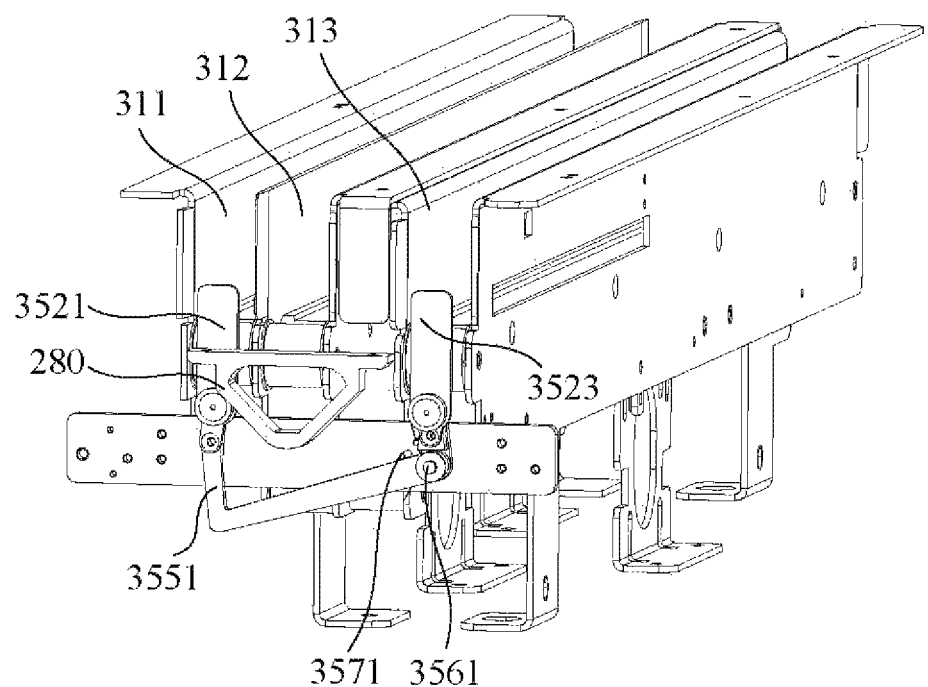
FIG. 21 is a schematic diagram showing a guide block is abutted against a roller from a right side of a first block piece in one embodiment.
Figure 22:
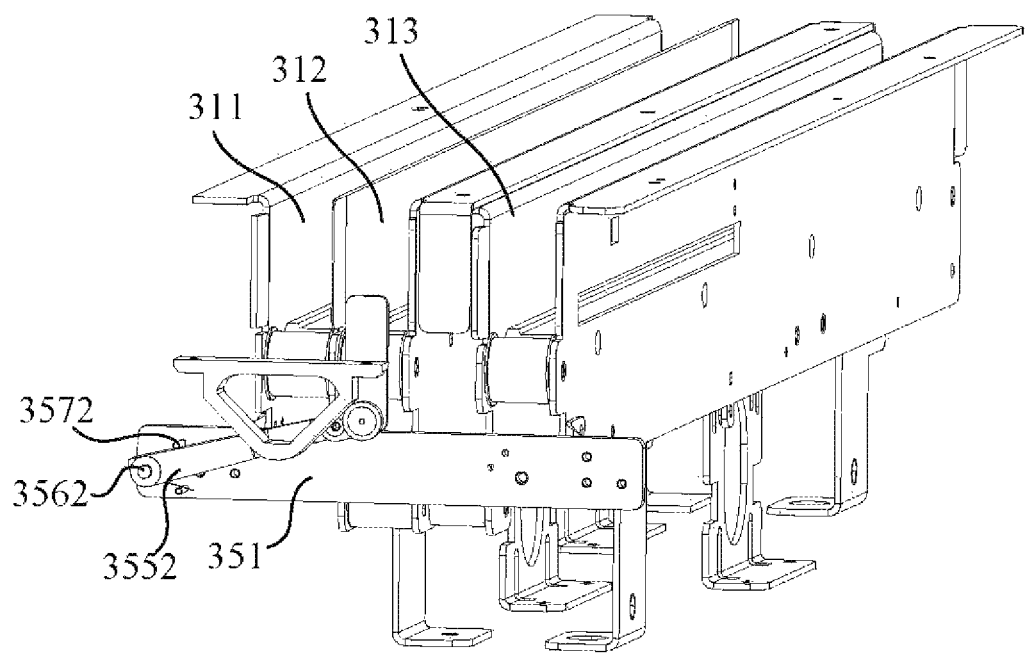
FIG. 22 is a schematic diagram showing a guide block is abutted against a roller from a left side of a second block piece in one embodiment.
Figure 23:
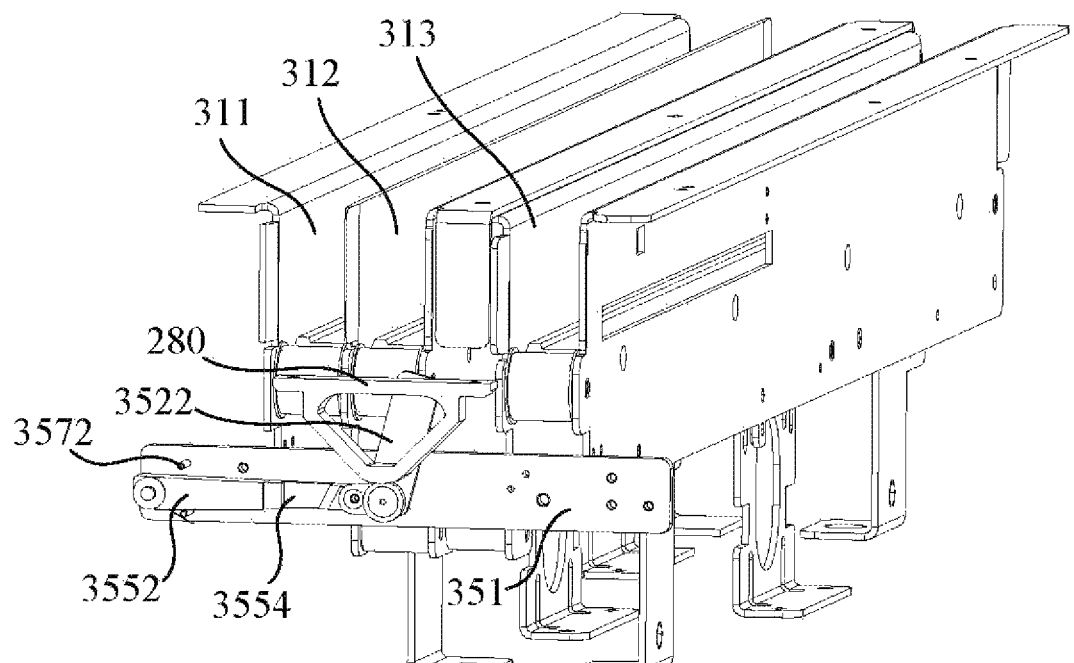
FIG. 23 is a schematic diagram showing a guide block is pressed against a second block piece in one embodiment.
Figure 24:
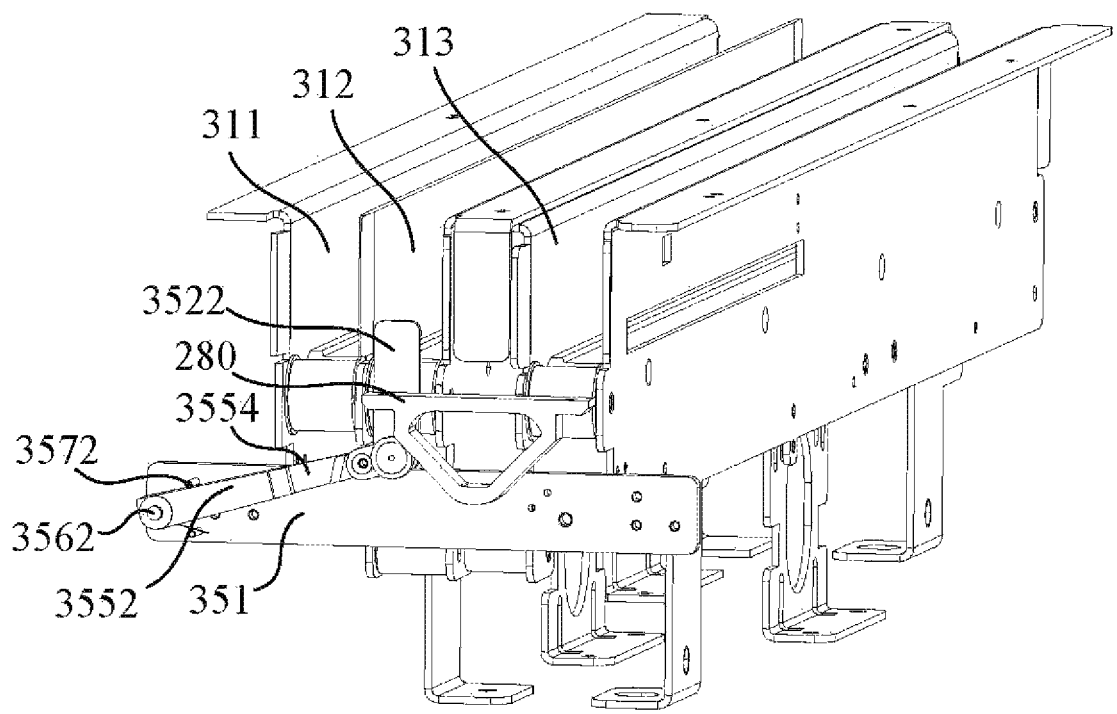
FIG. 24 is a schematic diagram showing a guide block is abutted against a roller from a right side of a second block piece in one embodiment.
Figure 25:
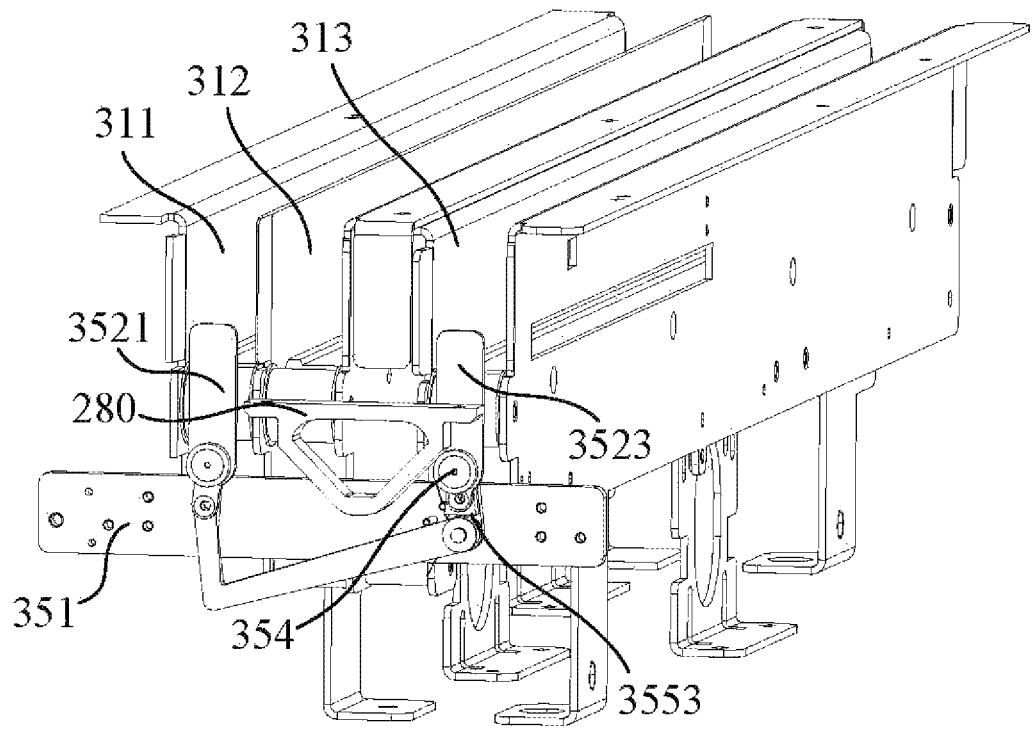
FIG. 25 is a schematic diagram showing a guide block is abutted against a roller from a left side of a third block piece in one embodiment.
Figure 26:
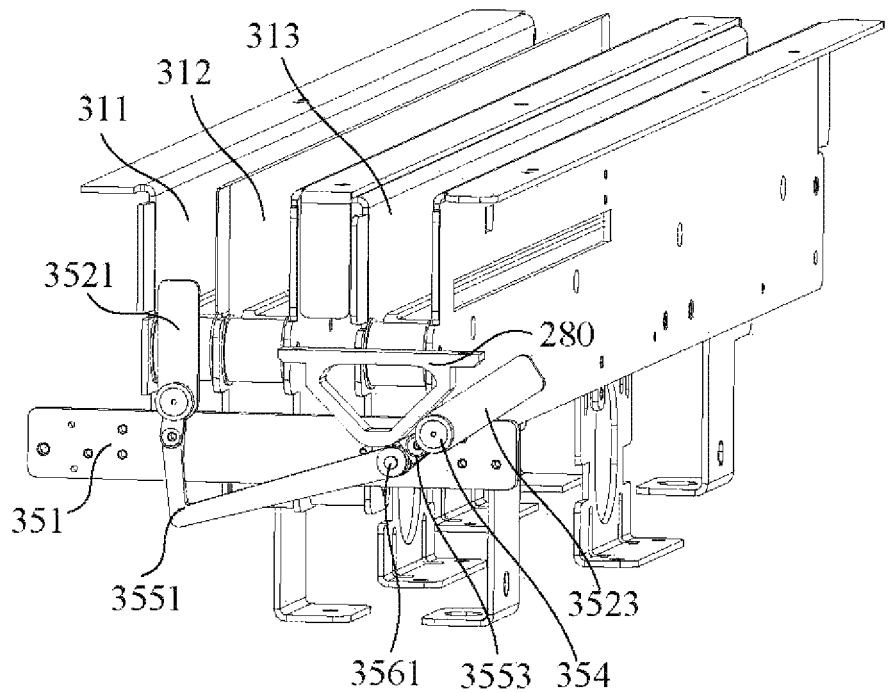
FIG. 26 is a schematic diagram showing a guide block is pressed against a third block piece in one embodiment.
Figure 27:
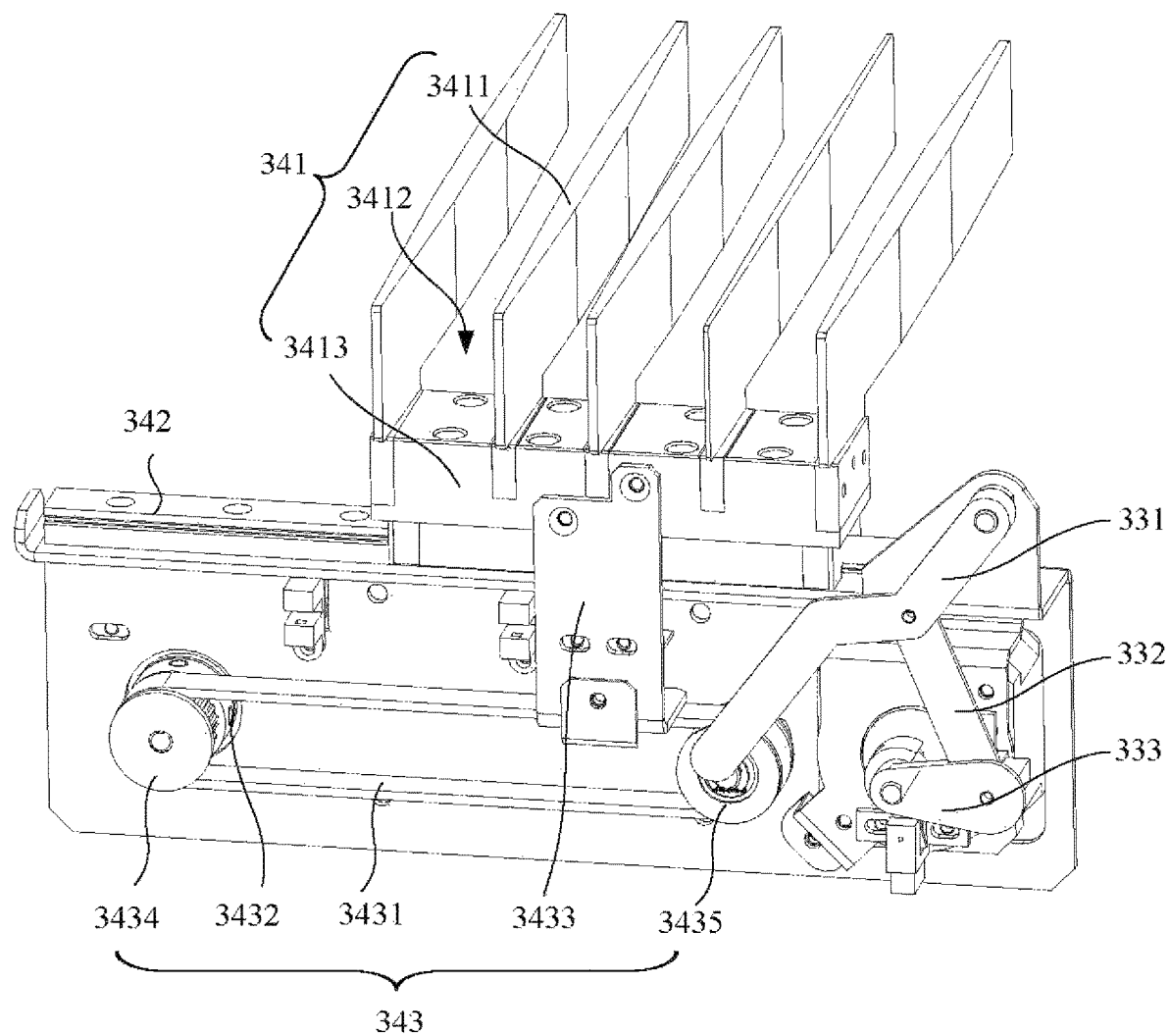
FIG. 27 is a structural schematic diagram of a rail changing mechanism in one embodiment.
Figure 28:
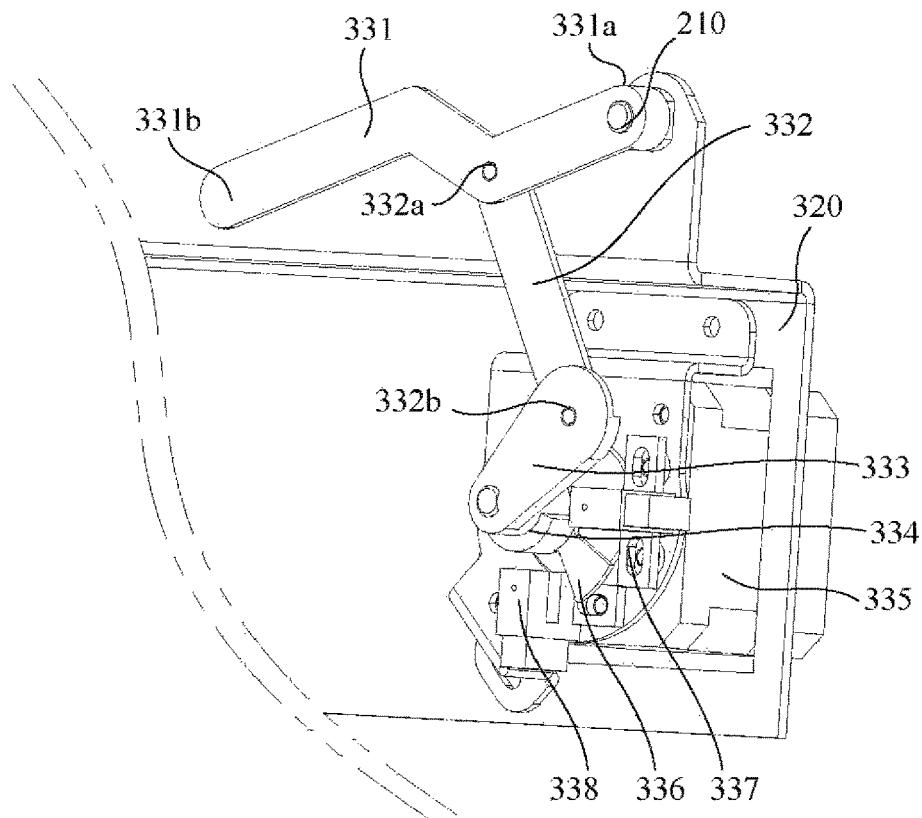
FIG. 28 is a structural schematic diagram of a transmission block mechanism in one embodiment.

With reference to FIG. 13, FIG. 27 and FIG. 28, in some embodiments, the transmission block mechanism 330 includes a block member 331, a connecting member 332 and a swing rod 333; one end 332a of the connecting member 332 is hinged with the block member 331, and the other end 332b of the connecting member 332 is hinged with the swing rod 333; the swing rod 333 drives the block member 331 via the connecting member 332 to rotate between a first position and a second position; a limit structure is arranged at the hinged place of the connecting member 332 and the swing rod 333, so that the block member 331 still can be kept at the first position with the interference of an external force.

Wherein, the first position is a position at which the block member 331 blocks the transmission passage, and the second position is a position at which the block member 331 unblocks the transmission passage.

In some embodiments, one end 331a of the block member 331 is rotationally arranged at one side of the transmission passage, and the other end 331b of the block member 331 can be rotated with the block member 331 to switch between the first position and the second position, thereby blocking or unblocking the transmission passage. Specifically, the one end 331a of the block member 331 is rotationally connected to the mounting seat 320. Through the mounting seat 320, the block member 331 is mounted at one side of the transmission passage.

In some embodiments, the swing rod 333 can be rotated around a rotating shaft 334 relative to the mounting seat 320, so as to drive the block member 331 via the connecting member 332 to rotate relative to the transmission passage.

In some embodiments, the transmission block mechanism 330 further includes a motor 335 or a cylinder configured to drive the swing rod 333 to swing around an axial line of the rotating shaft 334.

Figure 29:
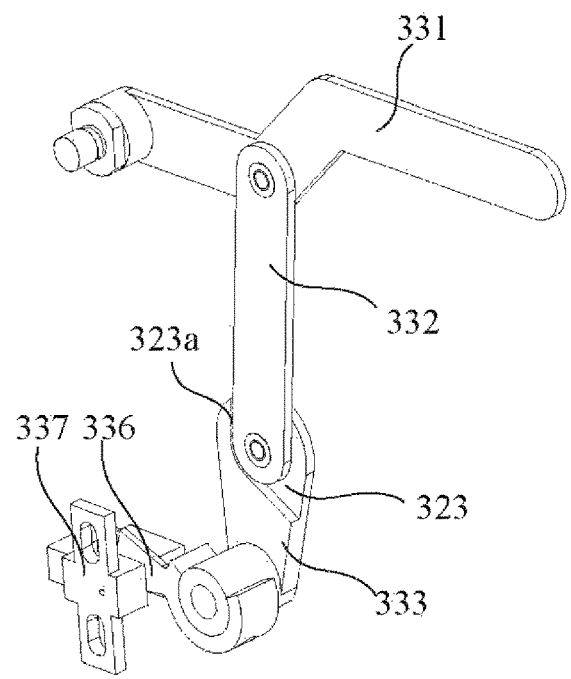
FIG. 29 is a schematic diagram when a block piece of a transmission block mechanism is located at a first position in one embodiment.

Simultaneously referring to FIG. 28 and FIG. 29, in some embodiments, a light barrier piece 336 is arranged on the swing rod 333. The mounting seat 320 is provided with an induction device in signal connection with the motor 335 or the cylinder. The induction device is arranged on a track that the light barrier piece 336 is moved with the swing rod 333. It may be understood that, the induction device may guarantee that the block member 331 is in the first position or the second position by detecting a rotation angle of the swing rod 333. In this embodiment, the induction device may include a first induction element 337 and a second induction element 338; when the first induction element 337 detects the light barrier piece 336, the block member 331 is in the first position; and when the second induction element 338 detects the light barrier piece 336, the block member 331 is in the second position.

Figure 30:
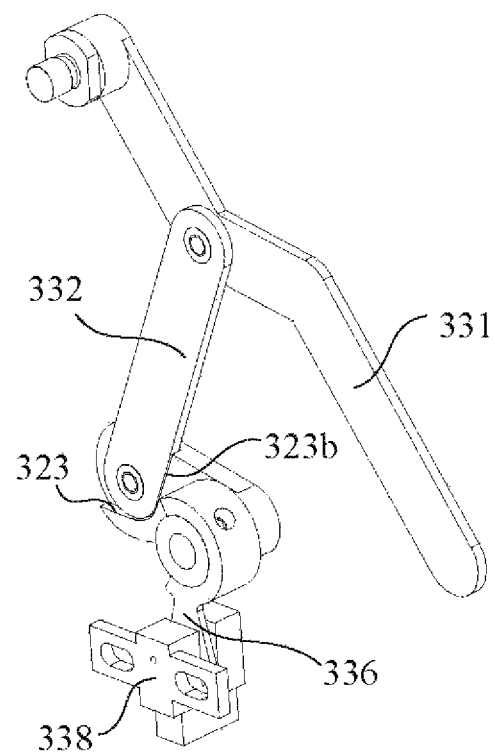
FIG. 30 is a schematic diagram when a block piece of a transmission block mechanism is located at a second position in one embodiment.

Simultaneously referring to FIG. 29 and FIG. 30, in some embodiments, the limit structure is a limit groove arranged on either of the connecting member 332 and the swing rod 333, and when the other of the connecting member 332 and the swing rod 333 is rotated to an extreme position in the limit groove, the block member 331 is in the first position or the second position. In this embodiment, the limit groove 323 is formed on the swing rod 333. The connecting member 332 is rotated between two lateral edges 323a and 323b of the limit groove 323 relative to the swing rod 333. Specifically, as shown in FIG. 29, when the connecting member 332 is swung to abut against the lateral edge 323a of the limit groove 323, the block member 331 is in the first position; and by blocking the sample racks 400 in the transmission passages of the rail component 310, the sample racks 400 are prevented slipping out from the rail component 310. As shown in FIG. 30 again, when the connecting member 332 is swung to abut against the lateral edge 323b of the limit groove 323, the block member 331 is in the second position and thus the transmission passages of the rail component 310 are in the unblock state; and thus, the sample racks 400 are moved via the rail component 310 to other structures or devices abutted with the rail component 310. When the rotation between the connecting member 332 and the swing rod 333 passes through a dead point and an included angle between the connecting member 332 and the swing rod 333 is an obtuse angle, a self-locking structure is formed between the connecting member 332 and the swing rod 333. Therefore, without an external force, the block member 331 may be kept at the first position and thus the excessive load of the device when the state of the block member 331 is kept using an external power source is avoided.

In other embodiments, the limit structure is a first limit edge and a second limit edge arranged on the connecting member 332 and/or the swing rod 333, and the connecting member 332 and the swing rod 333 are rotated oppositely between the first limit edge and the second limit edge; when the connecting member 332 and the swing rod 333 are stopped at the first limit edge or the second limit edge, the block member 331 is at the first position or the second position; and when the block member 331 is at the first position, the rotation between the connecting member 332 and the swing rod 333 passes through the dead point, the included angle between the connecting member 332 and the swing rod 333 is the obtuse angle and the self-locking structure also can be formed, the block member 331 is kept at the first position without the action of the external force and thus the sample racks 400 are blocked to pass through the transmission passages of the rail component 310 and the sample racks 400 are prevented from slipping out from the rail component 310.

It is to be noted that, in the above embodiment, the installation position of the transmission block mechanism 330 on the rail component 310 is not limited and may be arranged on an end portion or a middle portion of the rail component 310 according to an actual demand. Of course, it may be understood that, when the block member 331 of the transmission block mechanism 330 is at the first position, the sample racks 400 may be prevented from passing through the rail component 310, and the sample racks 400 are blocked at certain positions of the transmission passages of the rail component 310 so that other mechanisms or device can make further operation on the sample racks 400. And when the block member 331 is at the second position, the transmission passages of rail component 310 may continuously transmit the sample racks 400 to structure or devices abutted with the rail component 310.

In some embodiments, with reference to FIG. 12, FIG. 13 and FIG. 27, the rail changing mechanism 340 includes a shifting fork piece 341, a transverse guide rail 342 and a shifting fork driving mechanism 343; the shifting fork driving mechanism 343 is configured to drive the shifting fork piece 341 to transversely move along the transverse guide rail 342 at an sample rack output port of the transmission passage (perpendicular to an extension direction of the transmission passage), and thus the sample racks 400 are moved to other transmission passages and the sample racks 400 may be transmitted in different transmission passages. Specifically, the shifting fork piece 341 includes a plurality of push plates 3411 arranged at intervals; one ends of the plurality of push plates 3411 are slidably connected with the transverse guide rail 342 via a sliding seat 3413 and the other ends of the plurality of push plates 3411 are extended parallel to the extension direction of the transmission passage; and a notch 3412 into which the sample racks 400 may be moved is formed between adjacent push plates 3411. When the sample racks 400 are moved into the notch 3412 from one transmission passage of the rail component 310, the shifting fork driving mechanism 343 drives the shifting fork piece 341 to move along the transverse guide rail 342; and then, the push plates 3411 push the sample racks 400 to other transmission passages of the rail component 310 and the sample racks 400 may be transmitted in different transmission passages.

In some embodiments, the shifting fork driving mechanism 343 includes a synchronous belt 3431, a rail changing motor 3432, a connecting piece 3433, a driving wheel 3434 and a driven wheel 3435; the synchronous belt 3431 is sleeved on the driving wheel 3434 and the driven wheel 3435, the shifting fork piece 341 is connected with the synchronous belt 3431 via the connecting piece 3433; and the driving wheel 3434 is connected with an output shaft of the rail changing motor 3432. When the sample racks 400 need to be transferred to different transmission passages, the rail changing motor 3432 drives the driving wheel 3434 to rotate, and thus the synchronous belt 3431 drives the shifting fork piece 341 to move along the transverse guide rail 342 and the sample racks 400 are moved to different transmission passages for transmitting.

In some embodiments, the rail changing mechanism 340 and the transmission block mechanism 330 are mounted at a sample rack output port of the first transmission passage 311 via the mounting seat 320. In this way, when the sample racks 400 are transferred among different transmission passages, the sample racks 400 are blocked at the sample rack output port of the first transmission passage 311 by the transmission block mechanism 330 and are moved to the second transmission passage 312 or the third transmission passage 313 by the rail changing mechanism 340. It may be understood that, the first transmission passage 311 and the second transmission passage 312 may be a common sample adding passage and a quick sample adding passage in some specific applications. With the utilization of the quick sample adding passage, the analysis on some emergency samples is implemented. Upon this, the third transmission passage 313 may be used as a sample return passage. In this way, sample racks 400 in which a sample is detected or is taken away are returned to the transfer rail 220 of the sample rack transfer device 200 via the third transmission passage 313 and are transferred to the sample holder 110 of the sample rack storage device 100 via the sample rack transfer device 200, thereby implementing the circulation of the sample rack loading system.

In some embodiment, a chemiluminescence detector includes the sample rack loading system in the above embodiment.

In some embodiment, a sample rack loading method includes the following steps.

(a) A sample rack transfer device 200 is moved to one end of each of the transmission passages of the rail component 310, so that transfer rails 220 of the sample rack transfer device 200 are in abutment joint with the transmission passages of the rail component 310.

(b) A sample rack driving mechanism 250 transfers the sample racks 400 from the transfer rails 220 to the transmission passages of the rail component 310.

Wherein, in the step (a), the sample rack transfer device 200 is pressed against the block pieces 352 that block on the transmission passages, so that the block pieces 352 unblock the transmission passages. Hence, the sample racks 400 may be transferred from the transfer rails 220 to the transmission passages. Specifically, when the transfer rails 200 are abutted with the transmission passages, a guide block 280 arranged on the sample rack transfer device 200 is moved with the sample rack transfer device 200 to remove the block pieces 352 that block on the transmission passages and thus the transmission passages are unblocked.

In some embodiments, before the step (a), the loading method further includes the following steps.

(a1) The sample rack transfer device 200 is moved to the sample holders 110 of the sample storage device, so that the transfer rails 220 of the sample rack transfer device 200 are in abutment joint with the delivery ports 111 of the sample holders 110.

In the step (a) and/or the step (a1), the sample rack driving component 252 keeps a sample rack grabbing component 253 at the first end 230a of the rocker arm 230, so that the sample rack grabbing component 253 is pressed against the first end 230a of the rocker arm 230 and the second end 230b of the rocker arm 230 leaves away from the block mechanism 112. Hence, a block mechanism 112 blocks the delivery ports 111 of the sample holders 110, thereby preventing the sample racks 400 from slipping out to affect the operation of the device.

In some embodiments, after the step (a1) and before the step (a), the loading method further includes the following steps.

(a2) The sample rack driving component 252 of the sample rack transfer device 200 moves the sample rack grabbing component 253 of the sample rack transfer device 200 to be under the sample holders 110.

(a3) The sample rack grabbing component 253 locks the sample racks 400 in the sample holders 110.

(a4) The sample rack driving component 252 drives the sample rack grabbing component 253, thereby transferring the sample racks 400 locked by the sample rack grabbing component 253 to the transfer rail 220.

In the above embodiment, in the step (a2) to the step (a4), the sample rack driving component 252 moves the sample rack grabbing component 253 to leave away from the first end 230a of the rocker arm 230, so that the rocker arm 230 is rotated under the action of the reset component, the second end 230b of the rocker arm 230 is pressed against the block mechanism 112 and block pieces 1121 of the block mechanism 112 are removed from the delivery ports 111 of the sample holders 110; and thus the sample racks 400 are transferred from the sample holders 110 to the transfer rails 220 of the sample rack transfer device 200 under the action of the sample rack driving mechanism 250. Therefore, in this embodiment, when the sample rack driving mechanism 250 needs to transfer the sample racks 400 from the sample holders 110, the sample rack driving mechanism 250 will correspondingly remove the block mechanism 112 blocking the delivery ports 111 of the sample holders 110. In this sense, to select a state in which the block mechanism 112 unblocks the delivery ports 111, there is no need to independently arrange a control mechanism.

Each technical characteristic of the above embodiments may be combined freely. To describe concisely, all possible combinations for each technical characteristic of the above embodiments are not described. However, as long as there is no conflict among the combinations of these technical characteristics, all should be considered as a recording scope of the specification.

The above embodiments are only several embodiments of the present disclosure and are described concretely in detail, and therefore, should not be understood as limits to scope of the present disclosure. It should be noted that, those of ordinary skill in the art may further make several alternations and improvements without departing from the concept of the present disclosure, and all should be pertained to the scope of protection of the present disclosure. Therefore, the scope of protection of the present disclosure should be subjected to the appended claims.

What is claimed is:

1. A sample rack loading system, comprising:
a sample rack storage device, provided with a plurality of sample holders for storing sample racks, each of the sample holders being provided with a delivery port through which each of the sample racks is moved out or moved into;
a sample rack transmission device, comprising a rail component and a sample rack block piece mechanism; and
a sample rack transfer device, provided between the sample rack storage device and the sample rack transmission device so as to transfer the sample racks between the sample rack storage device and the sample rack transmission device, wherein
the sample rack block piece mechanism is provided at one side, close to the sample rack transfer device, of the rail component; the sample rack block piece mechanism is configured to block or unblock a transmission passage of the rail component; a guide block is provided on the sample rack transfer device; when a transfer rail of the sample rack transfer device is in abutment joint with the transmission passage, the guide block drives the sample rack block piece mechanism to unblock the transmission passage; and otherwise, the sample rack block piece mechanism blocks the transmission passage.

2. The sample rack loading system as claimed in claim 1, wherein each of the sample holders is provided with a block mechanism at the delivery port; the block mechanism comprises a first block piece and an elastic piece; the first block piece is provided with a first state at which the delivery port is blocked and a second state at which the delivery port is unblocked; the first block piece is kept at the first state under an action of the elastic piece; and by pressing against the first block piece, the first block piece can be placed at the second state.

3. The sample rack loading system as claimed in claim 2, wherein the block mechanism further comprises a rotary piece; the rotary piece is connected with each respective sample holder via a hinge piece; and the first block piece is extended from one end, close to the delivery port, of the rotary piece to an inside of the delivery port.

4. The sample rack loading system as claimed in claim 3, wherein the sample rack transfer device further comprises a mounting rack, a rocker arm, a reset component and a sample rack driving mechanism; through the mounting rack, the transfer rail is supported at one side of the delivery port; the rocker arm is rotationally connected to the mounting rack; the rocker arm is provided with a first end and a second end respectively located at two sides of a rotation axial line; the sample rack driving mechanism comprises a sample rack grabbing component and a sample rack driving component; the sample rack grabbing component is configured to pick up or release a respective sample rack among the sample racks; the sample rack driving component is configured to drive the sample rack grabbing component to move under the rocker arm; when the sample rack grabbing component is moved to the first end of the rocker arm, the sample rack grabbing component prods the first end of the rocker arm so that the second end of the rocker arm leaves away from the rotary piece of the block mechanism; and when the sample rack grabbing component leaves away from the first end of the rocker arm, the reset component drives the second end of the rocker arm to press against the rotary piece of the block mechanism.

5. The sample rack loading system as claimed in claim 4, wherein a suspension hole is formed at a bottom of each of the sample racks; the sample rack grabbing component comprises an electromagnet and an electromagnet ejector rod; and the electromagnet ejector rod can be moved telescopically up and down so as to lock and release a connection with the suspension hole.

6. The sample rack loading system as claimed in claim 4, wherein the sample rack transfer device further comprises an elastic-pressing rolling shaft mechanism; the elastic-pressing rolling shaft mechanism comprises a roller and an elastic pressing piece; the roller is connected with one side of the transfer rail via the elastic pressing piece; and the elastic pressing piece prestresses the roller so that a respective sample rack among the sample racks passing through the transfer rail is pressed against another side of the transfer rail.

7. The sample rack loading system as claimed in claim 4, wherein the reset component is a pressure spring or a tension spring; two ends of the pressure spring or the tension spring are respectively connected with the mounting rack and the rocker arm; and the second end of the rocker arm is pressed against the rotary piece of the block mechanism.

8. The sample rack loading system as claimed in claim 4, wherein the sample rack grabbing mechanism is slidably provided on a guide structure via a sliding seat; and the guide structure is provided on the mounting rack parallel to the transfer rail.

9. The sample rack loading system as claimed in claim 8, wherein a abutting inclined surface is provided on a top of the sliding seat; and when the sliding seat is slid to the first end of the rocker arm along the guide structure, the first end of the rocker arm is abutted against the sliding seat and is moved upward along the abutting inclined surface, and the second end of the rocker arm leaves away from the rotary piece of the block mechanism.

10. The sample rack loading system as claimed in claim 1, wherein the sample rack block piece mechanism comprises a mounting plate, a second block piece and an elastic element; the mounting plate is fixed at one side, close to the sample rack transfer device, of the transmission passage; the second block piece is connected with the mounting plate, and the second block piece can be moved between a blocking position and a unblocking position relative to the mounting plate; the elastic element is provided between the second block piece and the mounting plate, so that the second block piece and the mounting plate are elastically connected to place the second block piece at the blocking position; and when the sample rack transfer device is in abutment joint with the transmission passage, the guide block is abutted against the second block piece to place the second block piece at the unblocking position;

the blocking position is a position at which the second block piece blocks the transmission passage; and the unblocking position is a position at which the second block piece unblocks the transmission passage.

11. The sample rack loading system as claimed in claim 10, wherein a rolling element is connected outside the second block piece and under the transmission passage; slopes are provided at two sides of the guide block respectively; and when the guide block is translated to pass through the second block piece, the rolling element is abutted against the slopes and is slid along the slopes.

12. The sample rack loading system as claimed in claim 10, wherein the second block piece is rotationally connected with the mounting plate via a swing arm; and one end of the swing arm is connected with the second block piece, and the other end of the swing arm is provided on a rotating shaft of the mounting plate in a sleeving manner.

13. The sample rack loading system as claimed in claim 12, wherein the elastic element is a pressure spring or a tension spring; and two ends of the pressure spring or the tension spring are respectively connected with the mounting plate and the swing arm.

14. The sample rack loading system as claimed in claim 12, wherein the elastic element is a torsional spring provided on the rotating shaft in a sleeving manner; and the torsional spring is connected with the swing arm.

15. The sample rack loading system as claimed in claim 12, wherein a plurality of transmission passages are provided, and the sample rack bock piece mechanism comprises a plurality of second block pieces and a plurality of swing arms equal to the number of the transmission passages, and each second block piece blocks a respective transmission passage among the plurality of transmission passages; two adjacent swing arms of the plurality of swing arms are crossly provided on the mounting plate; and a groove is formed at a rotation track overlapped place on the two adjacent swing arms.

16. The sample rack loading system as claimed in claim 12, wherein the mounting plate is provided with a limit element; and the limit element is configured to keep the swing arm at the position where the second block piece blocks the transmission passage.

17. The sample rack loading system as claimed in claim 16, wherein the limit element is a limit pin; and the swing arm is rotated around the rotating shaft under an action of the elastic element and is at last abutted against the limit pin.

18. A chemiluminescence detector, comprising the sample rack loading system as claimed in claim 1.

19. A sample rack loading method comprising the sample rack loading system as claimed in claim 1, for transferring the sample racks from the sample rack storage device to the sample rack transmission device via the sample rack transfer device, wherein the sample rack block piece mechanism comprises a second block piece and an elastic element; the elastic element drives the second block piece to block the transmission passage; the sample rack transfer device further comprises a sample rack driving mechanism; the transfer rail can be in abutment joint with the delivery port and/or the transmission passage; and the sample rack loading method comprises the following steps: (a) moving the sample rack transfer device to one end of the transmission passage of the rail component, so that the transfer rail of the sample rack transfer device is in abutment joint with the transmission passage; and (b) transferring, by the sample rack driving mechanism, the sample racks from the transfer rail to the transmission passage; and in the step (a), the sample rack transfer device is pressed against the second block piece that blocks on the transmission passage, so that the second block piece unblocks the transmission passage.

20. The sample rack loading method as claimed in claim 19, wherein a block mechanism is provided at the delivery port; the block mechanism is provided with a first state at which the delivery port is blocked and a second state at which the delivery port is unblocked; when an elastic force of an elastic piece is overcome by pressing against the first block piece, the first block piece leaves away from the delivery port; the sample rack driving mechanism comprises a sample rack driving component and a sample rack grabbing component; the sample rack transfer device further comprises a rocker arm and a reset component; the rocker arm is provided with a first end and a second end capable of being rotated oppositely; the reset component drives the rocker arm to rotate, so that the second end of the rocker arm is pressed against the block mechanism and the block mechanism is in the second state; and the sample rack loading method further comprises the following step before the step (a):

(a1) moving the sample rack transfer device to the sample holders of the sample storage device, so that the transfer rail of the sample rack transfer device is in abutment joint with the delivery port of a respective, sample holder among the plurality of sample holders; and in the step (a1), the sample rack driving component keeps the sample rack grabbing component at the first end of the rocker arm, so that the sample rack grabbing component is pressed against the first end of the rocker arm and, the second end of the rocker arm leaves away from the block piece mechanism.

\* \* \* \* \*